United States Patent [19]

Begemann et al.

[11] Patent Number: 5,065,759
[45] Date of Patent: Nov. 19, 1991

[54] PACEMAKER WITH OPTIMIZED RATE RESPONSIVENESS AND METHOD OF RATE CONTROL

[75] Inventors: Malcolm J. S. Begemann, Velp; Bernhard de Vries, Dieren; Johannes S. van der Veen, Arnhem, all of Netherlands

[73] Assignee: Vitatron Medical B.V., Dieren, Netherlands

[21] Appl. No.: 575,289

[22] Filed: Aug. 30, 1990

[51] Int. Cl.$^5$ .............................................. A61N 1/365
[52] U.S. Cl. ........................................... 128/419.0 PG
[58] Field of Search ......................... 128/419 PG, 707

[56] References Cited

U.S. PATENT DOCUMENTS

| | | | |
|---|---|---|---|
| 4,228,803 | 10/1980 | Rickards | 128/419.0 PG |
| 4,428,378 | 1/1984 | Anderson | 128/419.0 PG |
| 4,503,857 | 3/1985 | Boute et al. | 128/419.0 PG |
| 4,527,568 | 7/1985 | Rickards | 128/419.0 PG |
| 4,622,980 | 11/1986 | Kunig | 128/707 |
| 4,702,253 | 10/1987 | Nappholz et al. | 128/419.0 PG |
| 4,860,751 | 8/1989 | Callaghan | 128/419.0 PG |
| 4,877,032 | 10/1989 | Heinze et al. | 128/419.0 PG |
| 4,884,576 | 12/1989 | Alt | 128/419.0 PG |
| 4,886,064 | 12/1989 | Strandberg | 128/419.0 PG |
| 4,905,697 | 3/1990 | Heggs et al. | 128/419.o PG |
| 4,926,863 | 5/1990 | Alt | 128/419.0 PG |
| 4,972,834 | 11/1990 | Begemann et al. | 128/419.0 PG |

FOREIGN PATENT DOCUMENTS 0222681 5/1987 European Pat. Off. ... 128/419.0 PG
2216011 10/1989 United Kingdom ...... 128/419.0 PG Primary Examiner—William E. Kamm
Attorney, Agent, or Firm—Woodcock Washburn Kurtz Mackiewicz & Norris

[57] ABSTRACT

A pacemaker system is provided for rate responsive pacing, wherein rate is controlled as a function of two or more sensor inputs, each sensor providing a signal representing a respective different control parameter. Preferably a first sensor signal represents a physiologically accurate although slow response signal such as OT interval, and a second sensor represents a relatively fast response such as activity. The two parameter signals are processed so that they are directly comparable and can be compared as indicators of pacing rate throughout the desired pacing range. The algorithm utilizes a parameter control reference curve for each respective parameter, such reference curve representing the desired correlation between pacing rate and the parameter signal. Rate control is accomplished by determining the difference between each processed parameter signal and its corresponding reference point for the current pacing interval, and logically analyzing the two differences to determine which is used to indicate change in pacing rate. Each parameter reference curve is automatically adjustable to correspond to patient conditions. Automatic drift correction of the fast response parameter, such as activity, is used to compensate for conditions where the fast response signal is not likely to be physiologically reflective of the patient condition.

49 Claims, 18 Drawing Sheets

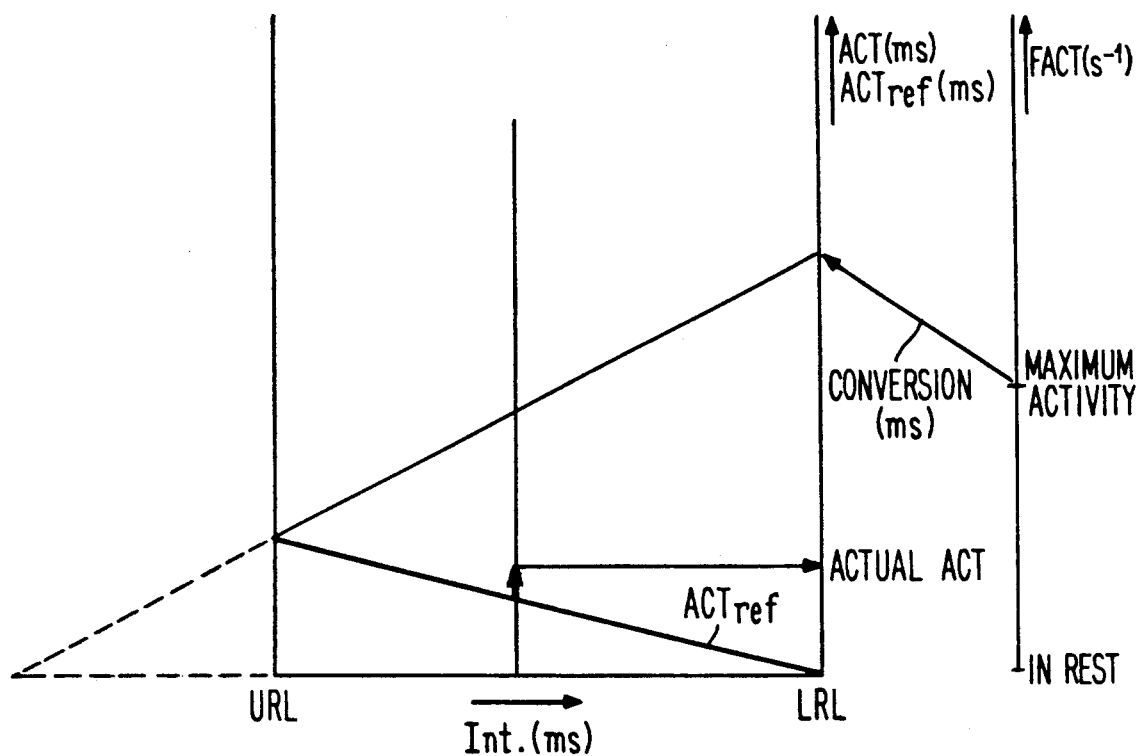
Fig. IIA
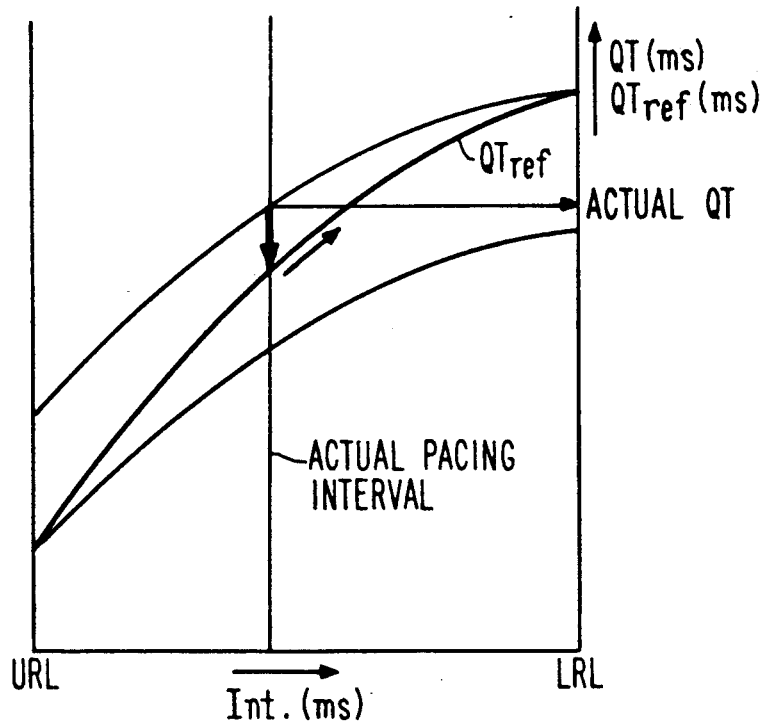
Fig. IIB

PACEMAKER WITH OPTIMIZED RATE RESPONSIVENESS AND METHOD OF RATE CONTROL

BACKGROUND OF THE INVENTION

1. Field of the Invention

The subject invention relates to cardiac pacemaker systems and, more particularly, implantable cardiac pacemakers which deliver pacing stimulus pulses at an adjustable rate based upon monitoring of patient conditions.

2. Description of the Background and Prior Art

Rate responsive pacemaker systems are widely available in the art. Rate responsive systems contain means for monitoring at least one patient variable and for determining an indicated pacing rate as a function of such sensed pacing variable, so as to control pacing rate optimally in terms of the patient condition. Such rate responsive pacemakers have gained wide acceptance as providing an improved response to the patient's physiological needs, as compared to programmable fixed rate pacemakers. Although atrial-based pacemakers, i.e. atrial synchronous or atrial sequential pacemakers, as well as DDD pacemakers, may in some patients provide an ideal form of rate responsiveness, such pacemakers are not satisfactory for many patients with cardiac conditions.

A number of patient variables or rate control parameters have been suggested in the technical literature and used commercially. One of the first physiological parameters utilized for rate control is the QT interval, as disclosed in the U.S. Pat. No. 4,228,803 to Rickards, and the U.S. Pat. No. 4,305,396 to Wittkampf et al. The QT interval is in fact the interval between a delivered pacing stimulus and the subsequent evoked T-wave, and has been utilized as the parameter indicative of physiological demand for heart output, and thus pacing rate. Additionally, activity sensors have been widely utilized for detecting the general activity level of a patient with a pacemaker, and for controlling the pacing rate or escape interval in response to detected activity level. See the U.S. Pat. No. 4,428,378 to Anderson et al. Other parameters which have been utilized or investigated for suitability as controlling pacing rate include respiration rate, thoracic impedance changes, venous blood temperature, pH, oxygen saturation and stroke volume.

In addition to the selection of a desired monitored parameter, and the corresponding sensor to be used, the algorithm utilized by a pacing system is of great importance. An example of an improved rate adaptive algorithm used in a pacing system is set forth in U.S. Pat. No. 4,972,834, Ser. No. 252,653, filed Sept. 30, which discloses a QT pacemaker with dynamic rate responsiveness, incorporated herein by reference. As set forth in this referenced patent, the algorithm which correlates the monitored or sensed parameter with indicated pacing rate may be adapted as a function of history, and particularly can be readjusted with respect to limits such as lower rate limit (LRL) and upper rate limit (URL).

Another approach to optimizing rate responsiveness is to use dual or plural sensors, in order that the drawbacks or deficiencies of a given sensor and/or algorithm may be compensated by the use of a second or other sensors having different characteristics. This approach is set forth in the patent to Rickards, U.S. Pat. No. 4,527,568, which discloses switching control of rate responsiveness from one monitored parameter, e.g. atrial rate, to another control parameter, e.g. QT interval. There are many other examples of dual sensor approaches in the literature, and reference is made to U.S. Pat. Nos. 4,926,863 and 4,905,697. These references are characterized by designs which switch control from one sensor to another, or from one algorithm to another, depending upon monitored values of the rate control parameters. While this approach may produce increased efficiency and improvement over the single sensor approach, it still does not provide a continuous optimization of information such as is potentially available from two or more sensors, so as to continuously optimize and adapt the actual pacing rate for all foreseeable conditions. As used in this specification, "sensor" or "sensor means" refers to any means for obtaining a control parameter, including the lead means such as is used for obtaining the QT interval, or other sensors such as in use for detecting body activity and the like. The techniques for sensing rate control parameters, and developing and processing therefrom signals useful for pacemaker control, are well known in the art.

A longstanding unsolved problem in this art area, for which there is a need for improvement, is thus to provide either a sensor or combination of sensors which more nearly fulfills the requirement of the ideal rate adaptive system. For example, a rate adaptive system should provide a quick and accurate initial response to situations such as start of exercise. The QT interval, as a rate control parameter, provides only a gradual response, as compared to an activity sensor which provides a fast, i.e., quick response. Another requirement is that the parameter or parameters chosen should provide an indication of pacing rate which is proportional to the work load. The QT interval provides a very good indication of work load, whereas the activity sensor approach is not as good, and may be subject to false indications. Another important requirement for a rate control parameter is specificity, i.e., that the characteristics of the parameter signal are specific to the conditions of rest and exercise of the patient and are thus physiologically appropriate. For example, the QT interval has a high specificity, whereas activity as a parameter has a medium specificity. Yet another requirement is providing an optimum indication of rate decrease following cessation or reduction of the condition compelling higher rate, such as exercise. It is important that the speed of rate decay after the cessation of exercise be properly related to the patient's physical condition. It is known that a patient in relatively poor physical condition experiences a slow decrease of the heart rate after exercise, while a person in relatively good physical condition experiences a more rapid decrease of the heart rate after exercise. A pacemaker controlled by an activity sensor is less than optimal in this regard, since a cessation of exercise results in a sharp drop in the activity signal which, if not modified, would lead to a non-physiological step-like reduction in pacing rate. As a consequence, it is necessary to program a fixed time period for gradually decreasing the pacing rate when the activity sensor stops delivering information calling for a higher rate. The pacemaker which is controlled by the QT interval exhibits the inverse relationship as known from exercise physiology, but tends to provide too slow a pacing rate decay.

What is thus sought in this art area is a pacer having two or more sensors and an algorithm for deriving information from each so as to optimize the determination of desired pacing rate. At the start of exercise, for example, it is desired to have the algorithm force an initial but limited fast rate increase. Thereafter, it becomes important to ensure that the pacing rate correlates proportionally to work load, and that if continuous exercise is not confirmed, the pacing rate will slowly decrease toward a lower limit. The algorithm, combined with the sensing means, should also force a faster, although limited rate decrease when stop of exercise is detected, with further rate decrease following the physiologically inverse relationship.

As is well known, the microprocessor and logic circuit technology for dealing with these problems in a pacemaker environment is available. What is needed is a pacemaker system which utilizes this technology so as to optimize the translation of plural sensor information into pacing rate control.

SUMMARY OF THE INVENTION

The pacing system of this invention provides an improvement in rate responsive pacemakers so as to more optimally adapt rate control to patient conditions. Specifically, the object is to combine information from two or more sensor sources so that during all phases of the patient's activity and rest there is provided information accurately reflective of the physiological state of the patient, as well as fast response information from which more appropriate time control of pacing rate can be derived and accomplished.

A specific object of this invention is to provide a pacing system which is rate responsive to a quick response sensor which monitors a parameter such as activity, as well as a slower response sensor which monitors a more specific parameter such as QT interval, having an algorithm and control means for detecting which sensor source provides the optimum information under any given patient condition, and controlling pacing rate in response to the detected optimum information so as to provide physiologically optimal pacing.

It is a further object of this invention to provide rate control pacing where the pacing rate is primarily controlled in response to first sensor information which is highly specific to patient physiological conditions and provides an indication proportional to work load, and wherein the controlled pacing rate is modified according to further information from one or more other sensor sources which provide a quicker response to patient conditions, than does the first sensor source.

It is yet a further object of this invention to provide an inplantable pacemaker which is rate controlled as a function of at least two parameters reflective of patient condition, the pacemaker utilizing an algorithm adapted to provide primary control on the basis of a first of said parameters, and having means for adjusting and coupling the control information derived from the second parameter so as to be adapted for use in the same algorithm, thereby giving the pacemaker the advantage of continual comparison of comparable information from at least two parameter sources for logically deciding what pacing rate is appropriate.

In accordance with the above objectives, there is provided a pacemaker system and method of controlling pacing rate wherein at least two rate control parameters are utilized. The system incorporates means for processing a second one of the parameter signals so that the respective parameter signals are comparable, i.e. can be compared by a logic analysis as part of an algorithm in determining how to control pacing rate. This system includes establishing parameter control reference curves for each respective parameter, each reference curve representing pacing rate (or pacing interval) as a function of the respective parameter signal, and each of the two or more parameter curves being coupled so that each parameter indication is logic comparable over a range of pacing rates. Primary rate control is based on a first parameter such as QT interval, and rate control is modified by information from a secondary source such as an activity sensor. Each reference parameter curve is automatically adjustable to correspond to patient conditions and patient history, while maintaining the curves coupled. Automatic drift correction of the secondary parameter, such as activity, is used where there is a difference between the variable and its corresponding reference curve point whereby one can choose to correct only positive differences, only negative differences or both, so as to maintain comparability of the variables, permitting continuous interval-to-interval comparing and decision making on rate control.

BRIEF DESCRIPTION OF THE DRAWINGS

FIGS. 11A and 11B illustrate graphically a fifth situation where the algorithm indicates a decreased rate.

DESCRIPTION OF THE PREFERRED EMBODIMENTS

Figure 1:
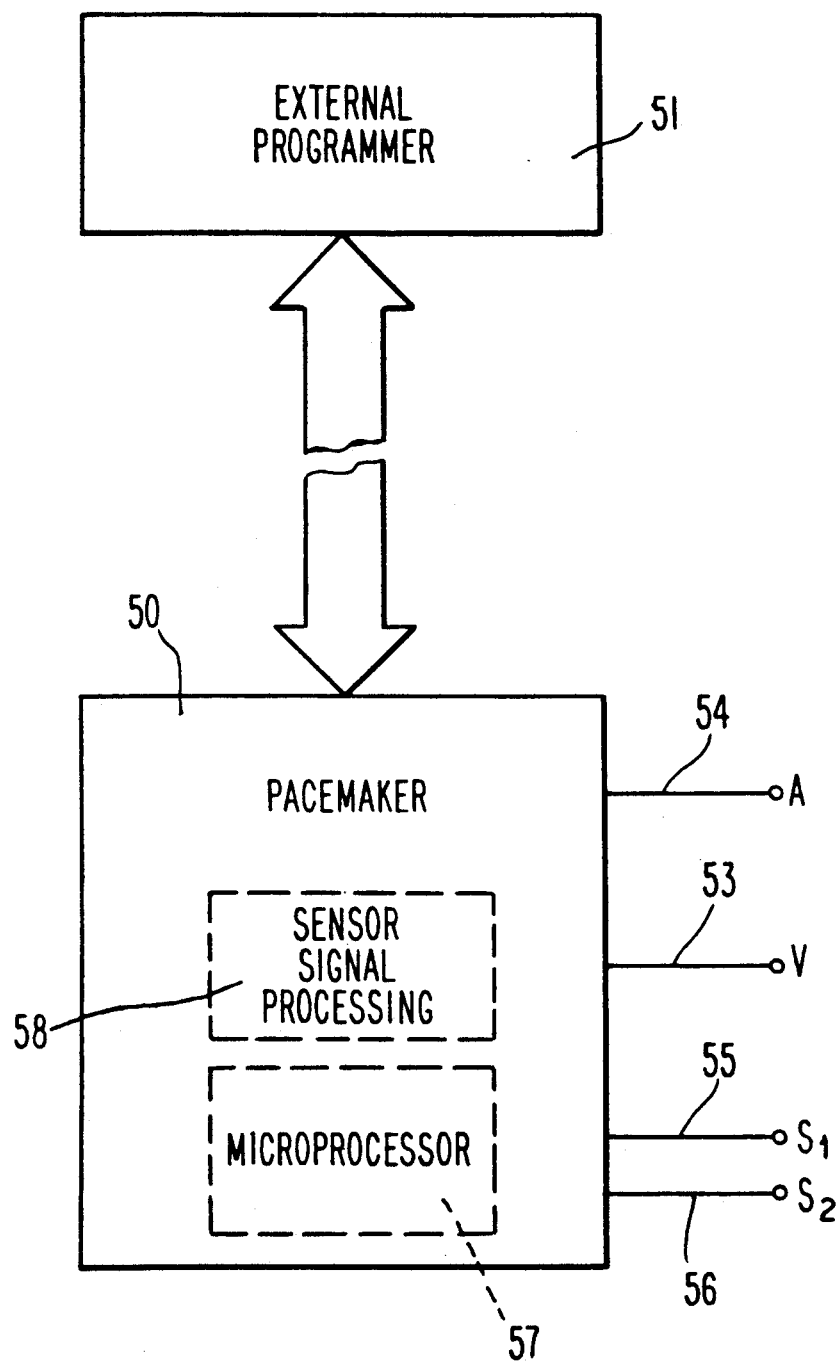
FIG. 1 is a schematic block diagram of a pacing system with microprocessor control, such as can be used for this invention.

In discussing the pacemaker system of this invention, reference is made to the prior art which teaches the use of microprocessor capability in an implantable pacemaker system, as well as the art of external programmer communication with an implanted pacemaker. Reference is made to U.S. Pat. Nos. 4,527,568 and 4,503,857, incorporated herein by reference, which describe operations of pacemaker embodiments incorporating microprocessor logic and software algorithms. U.S. Pat. Nos. 4,228,803 and 4,305,396 describe the operation of embodiments of a Tx pacemaker, i.e., one which is rate responsive to the QT interval, and are incorporated by reference. Generally, the prior art teaches and discloses various means of using microprocessors and software in controlling the operation of an implanted pacemaker. Accordingly, the specification does not contain a detailed description of the commercially available and known techniques of programming a microprocessor, storing data in memory and retrieving it, carrying out such operations as timing time intervals and setting up sensing windows, the logic of resetting the escape interval when a natural heartbeat is sensed, etc. These operations are well known in the art and are taught by the above references as well as other published patents and articles in this area. Reference is also made to the commercially available ACTIVITRAX pacemaker, of Medtronic, Inc. and the QUINTECH pacemaker of Vitatron Medical B.V., as commercial embodiments of software controlled pacers which are rate responsive to activity and QT interval respectively, and to the literature describing these pacemakers.

The following Glossary defines terms which are referred to in the description of the preferred embodiments:

GLOSSARY OF TERMS

ACT: Control parameter representing activity $ACT_{ref}$: Reference value of activity control parameter at a given interval (pacing rate)

$ACT_{dif}$: $ACT_{ref} - ACT$

ACTdr: Drift factor used to adjust

ACTmpl: Conversion factor by which activity counts (Nact) is multiplied to convert to units of ms B: second order constant in polynomial relating $QT_{ref}$ to interval; primary factor in determining value of $QT_{ref}$ at URL Dact: value of incremental change in $ACT_{ref}$ for decremental change in interval Dpt: first order in polynomial relating to $QT_{ref}$ and interval; value of incremental change in $QT_{ref}$ for incremental change in interval Fact: Activity frequency for activity sensor Int: Pacing interval in ms LRL: Lower rate limit of pacing range N: Number of intervals or number of 3.3 second periods counted in determining Nact Nact: Number of counts of activity sensor QT: Interval between delivered pacing pulse and evoked T wave; also referred to as QT interval.

$QT_{ref}$: Value of QT reference curve corresponding to a given interval (Ttx).

$QT_{dif}$: $QT_{ref} - QT$ $QT_{STR(max)}$: Maximum difference in QT due to increase in stress, i.e., difference in QT at a given interval as between patient at rest and patient at maximum exercise.

$QT_{max}$: Lowest value of QT for a patient at maximum exercise and URL

QT(m): Maximum value of QT at LRL and patient at rest

QTsave: $QT_{ref}$ − CRVMAX

Ttx: Interval on $QT_{ref}$ and $ACT_{ref}$ curves corresponding to pacing interval TwA: Amplitude of T wave $T_{URL}$: Interval at upper rate limit $T_{LRL}$: Interval at lower rate limit URL: Upper rate limit of pacing range LOOP: Software number corresponding to step size of increase in pacing interval CRVMAX: Programmable value representing threshold change in QT at URL for determining whether $QT_{ref}$ should be changed at URL In the subject invention, the improvement lies primarily in an algorithm for processing data from two or more sensor sources, so as to optimize rate control. The algorithm is structured so as to go through routines each pacing cycle, making rate change decisions based on a comparison of indications from each of the sensors. In the preferred embodiment as illustrated, pacing rate is adjusted each cycle, or interval, but the invention is not so limited. Thus, the principles of the invention can likewise be applied to adjusting pacing rate every N cycles, every elapsed predetermined time period, etc. Also, while the preferred embodiment illustrates a two sensor mode where the pacemaker is responsive to QT and activity information, it is to be understood that other combinations of two or more sensor inputs may be utilized. As used herein, sensor, or parameter sensor, broadly refers to obtaining rate control information and processing for use as control signals, and embraces systems such as the QT system where the pacing lead is utilized, as well as other systems where two or more separate sensors are utilized.

Referring to FIG. 1, there is shown a schematic representation of a pacer system as utilized in this invention. A pacemaker, preferably an implantable pacemaker 50, is used with an external programmer 51, the external programmer operating in a known manner to program pacemaker variables. A lead 53 is illustrated as being a ventricular lead, which lead delivers stimulus pulses to the ventricle and also provides sensed patient heartbeat signals to the pacemaker in a known manner. A lead 54 may also be used for a dual chamber pacemaker, connecting the pacemaker to the atrium. Leads 55 and 56 are shown connected to sensors S1 and S2 in the patient, for providing control parameters as discussed above. For a system using the QT and activity parameters, only leads 53 and 55 would be required. The pacemaker is illustrated as having a microprocessor 57, which includes memory for carrying the software of the algorithm of this invention. A block 58 is also indicated for signal processing of signals derived from lead 53 and sensors S1 and S2 in the known manner. The pacemaker contains the conventional means for generating stimulus pulses, inhibiting on demand, controlling rate, pulse width, etc.

By way of overview, the algorithm of the preferred embodiment of this invention is based upon several principles, or premises. A first working premise is that one of the parameters is taken as the primary control parameter, e.g. QT, and the other parameter is converted into corresponding units so as to be comparable for control purposes. Thus, in the preferred embodiment the ACT variable is derived by first obtaining counts from an activity sensor. See U.S. Pat. No. 4,428,378, incorporated herein by reference. The count is converted into a variable having units of ms, the same as QT, and is adjusted by a multiplier factor so as to provide a comparison of the two variables throughout the anticipated pacing range between lower rate limit (LRL) and upper rate limit (URL).

Another principle of the algorithm of this invention is that a reference curve is established for each variable, the reference curve establishing desired correlation of the control variable and the pacing interval. Actual control of pacing is preferably accomplished on the basis of the determined difference between the value of each respective control parameter at a given interval compared to the corresponding reference value of that parameter at the point on the reference curve corresponding to the pacing interval. Thus, for the QT parameter, the algorithm operates each interval to determine the difference between the QT reference value ($QT_{ref}$) for the pacing interval and the measured QT, to get $QT_{dif}$. Likewise, the algorithm makes a determination of the difference between the activity reference ($ACT_{ref}$) and the determined ACT parameter, to obtain a value of $ACT_{dif}$. Change of pacing rate, which in the preferred embodiment is accomplished each interval or pacing cycle, is determined as a function of these difference values, and not as a function of a comparison of the variable for the current interval versus the variable for the prior interval. Each interval, or cycle, the reference value for each pacing parameter is updated, or adjusted. Thus, for each new interval, the corresponding reference value is either incremented or decremented in accordance with a predetermined formula which establishes the reference curve for each respective parameter.

The reference curves are coupled in the sense that each reference curve represents a predetermined relation, or correlation, between pacing interval and its respective parameter between LRL and URL. In a preferred embodiment, the reference curve for the primary parameter, QT, is established in accordance with measured patient response to stress, and the second reference curve is scaled with respect to the first reference curve in a manner such as to adjust the influence of each parameter in determining control of pacing rate. Thus, the invention embraces the use of two or more control parameters, and an algorithm for establishing a respective reference curve for each such parameter. The reference curves are coupled so as to represent respective predetermined relationships between pacing rate and the control parameters between the programmable rate limits of the pacemaker, the algorithm determining change in pacing rate as a function of determined differences between each parameter and its respective reference value at the current pacing interval in accordance with predetermined logic.

Figure 2:
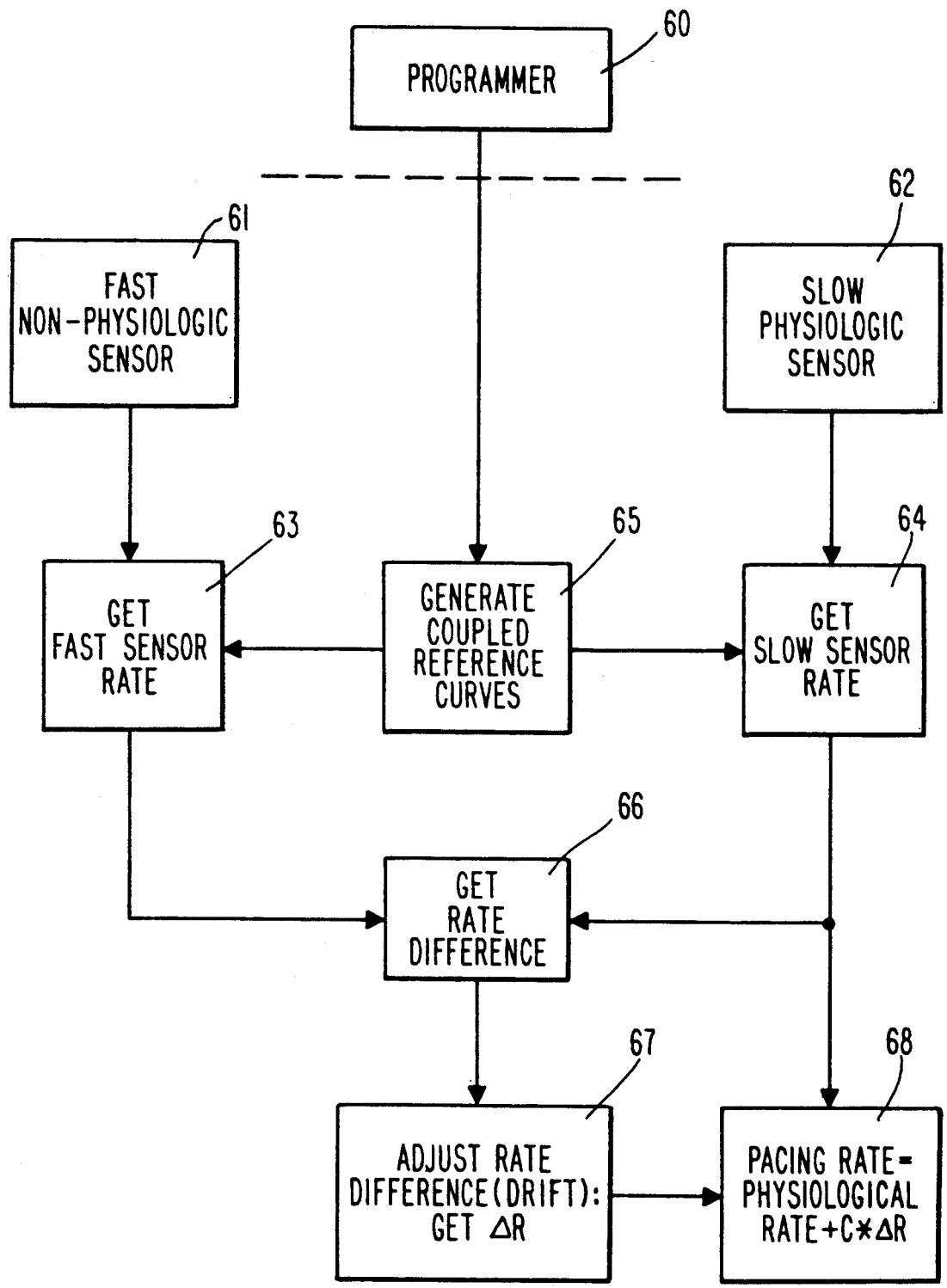
FIG. 2 is a generalized flow diagram showing some of the main features of the system and method of this invention.

Referring now to FIG. 2, there is shown a generalized flow diagram which represents the basic steps of the algorithm of this invention for determining pacing rate as a combined function of two control parameters derived from separate sensor sources. An external programmer 60 communicates with the pacemaker device. In general, the programmer is used for programing different pacing operating constants as is conventional in the use of programmable pacemakers. In this case, the programmer provides data which is used for generating the coupled reference curves, as indicated in block 65. A fast non-physiological sensor, such as an activity sensor, is indicated at block 61, and provides a signal which is operated on to get a fast sensor rate indication, as indicated at block 63. Note that the step of obtaining the fast sensor rate utilizes reference curve information, i.e., the sensor indication is compared to the reference information and the difference is used to determine the fast sensor rate. Likewise, a slow physiological sensor, such as means for obtaining the QT interval, is indicated at 62. Its output is processed at 64 to get a slow sensor rate, utilizing the correlation information generated at block 65. The fast sensor rate and the slow sensor rate are compared at 66, and the rate difference is adjusted at block 67. This adjustment constitutes changing the difference by a drift factor to get a differential adjustment indicated as $\Delta R$. At block 68, the pacing rate is determined as the physiological rate (the slow sensor rate) plus an increment determined by multiplying $\Delta R$ by a factor C. Thus, the pacing rate is determined as a primary function of the physiological, or slow rate, and adapted as a function of the fast sensor rate, the adaptation being adjusted by the drift factor. It is to be understood that the adjustment of the contribution of the secondary sensor may be obtained by different procedures other than the drift factor as used herein, e.g., by differentiation of the rate difference or another mathematical operation.

As used herein, drift refers to a periodic change in the contribution of the fast, or secondary sensor rate. For example, where the fast sensor indicates a rate higher than the physiological rate, such that the value of $\Delta R$ is positive, the pacemaker may decrement the positive value of $\Delta R$ once every predetermined number of seconds, causing $\Delta R$ to drift toward zero and thus reduce over a period of time the differential effect of the fast sensor. Likewise, where the $\Delta$ rate is negative, meaning that the pacing rate is below the physiological rate due to the contribution of the fast sensor rate, the drift factor would increment $\Delta$ rate so that the negative $\Delta$ rate drifted toward zero with time. The effect of introducing such a drift factor is thus to initially permit the influence of the fast sensor on the premise that its fast response is more accurate than that of the slow sensor in reacting to changes, but to diminish with time the differential influence of the fast sensor on the grounds that after a while the slow sensor is more reliable. By only allowing a decremental drift of $\Delta R$ or only an incremental drift of $\Delta R$ one can choose to only diminish rates which are higher or lower than the physiological rate.

Figure 3:
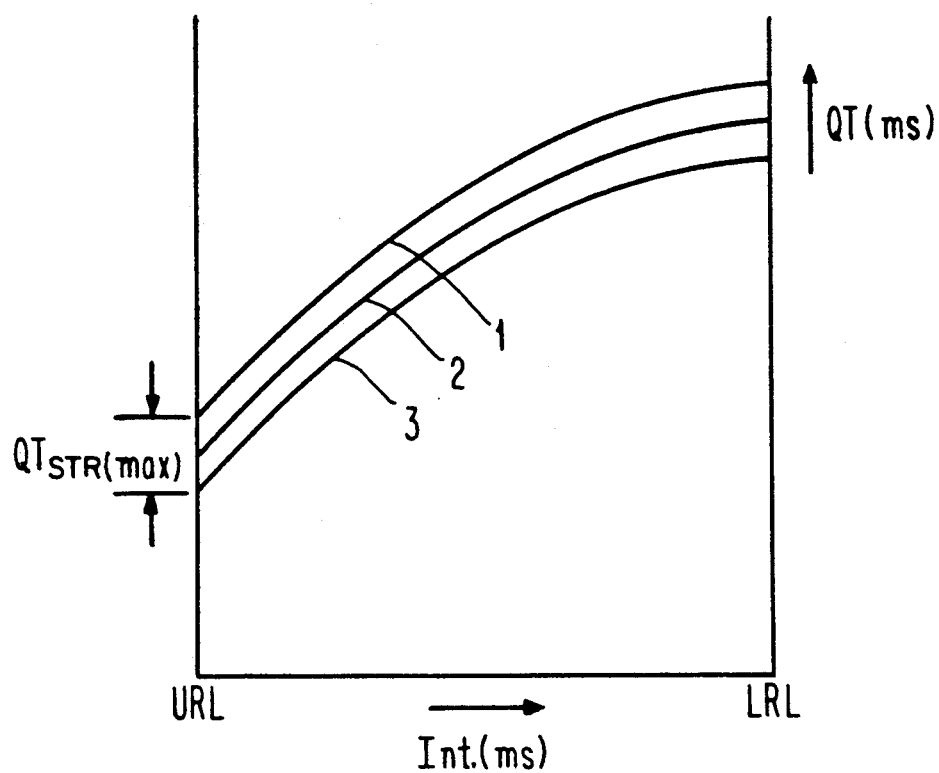
FIG. 3 shows a set of curves representing QT as a function of pacing interval for different patient stress levels.

It is known that the QT interval is in fact influenced both by the pacing interval and by mental and physical stress. Thus, when the pacing interval shortens, QT shortens likewise, and vice versa, in a non-linear manner. Both mental and physical stress cause QT to shorten, and for this invention it is assumed that the relation between stress change and QT change is substantially linear. FIG. 3 shows curves for this relationship corresponding to the patient at rest (1), medium exercise (2) and maximum exercise (3). $QT_{STR(max)}$ indicates the change in QT at URL between rest and maximum exercise. The QT interval is obtained in the ordinary manner, with circuitry and/or software for timing out the interval between the delivered stimulus pulse and the sensed T wave. See, for example, U.S. Pat. No. 4,527,568.

Figure 4:
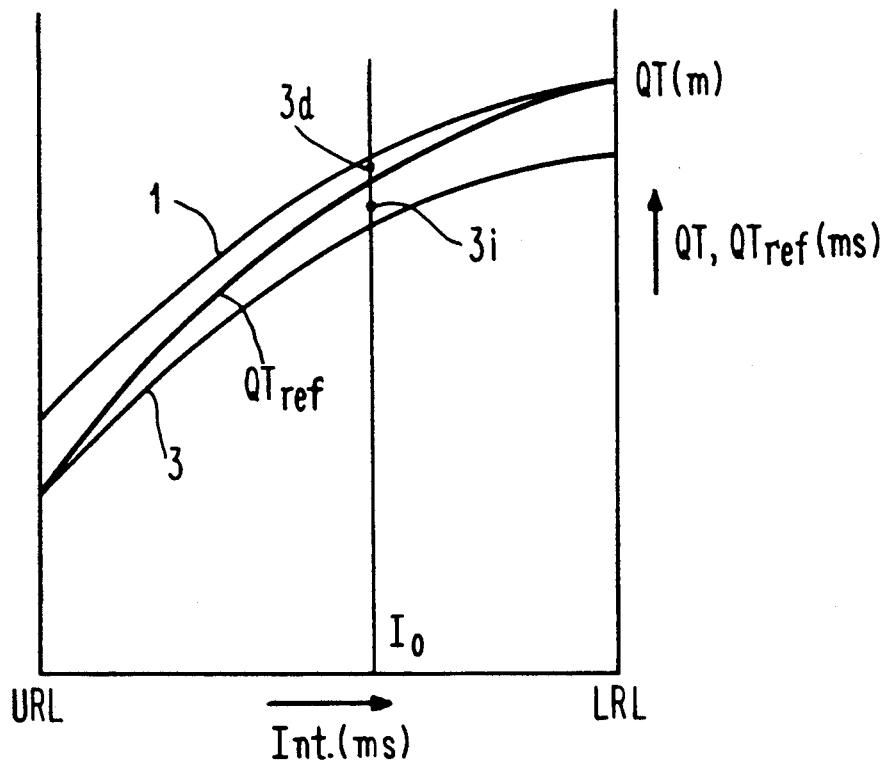
FIG. 4 shows the QT reference curve ($QT_{ref}$), which is a function of pacing interval, in relation to curves of QT for rest and maximum exercise.

The $QT_{ref}$ curve, which correlates QT as a function of interval, is illustrated in FIG. 4. The $QT_{ref}$ curve must be maximum at LRL and zero stress (patient in rest condition) and must be minimum at URL and maximum stress (maximum patient exercise). The $QT_{ref}$ curve between these two limits is chosen such that the relation between $QT_{ref}$ and interval is a second order polynomial function, providing that the step change in $QT_{ref}$ is a linear function of interval:

$$QT_{ref} = QT(m) - Dpt(T_{LRL} - int) - B'(T_{LRL} - int)^2$$

$$\Delta QT_{ref} = -Dpt - B(T_{LRL} - int)$$

FIG. 4 illustrates the determination of $QT_{dif} = (QT_{ref} - QT)$ at a given interval. Thus, if at the pacing interval designated $I_o$, the actual QT is less than the reference curve, as indicated at point 3i, then $QT_{dif}$ is greater than 0, indicating a desired increment in the pacing rate (decreasing pacing interval). On the other hand, if the measured QT is greater than the reference value, then $QT_{dif}$ is negative, indicating a decrease in pacing rate (increase in interval). This is summarized as follows:

| Point 3i: | $QT < QT_{ref}$ |
| --- | --- |
| | $QT_{dif} = (QT_{ref} - QT) > 0$ |
| | increment pacing rate |
| Point 3d: | $QT > QT_{ref}$ |
| | $QT_{dif} = (QT_{ref} - QT) < 0$ |
| | decrement pacing rate |

To obtain the second pacing parameter (ACT) a piezo-electric element (which may be S1 in FIG. 1) is suitably glued inside the pacemaker can. The activity sensor delivers an electrical signal that depends on vibrations of the can, which in turn are caused by movements of the patient and thus relate to exercise. The electrical signal is sensed by a sense amplifier, and the number of activity senses is counted. This number, Nact, is assumed to be proportional to the physical stress, and thus a measure thereof. Reference is made to U.S. Pat. No. 4,428,378, assigned to Medtronic, Inc., which discloses a rate adaptive pacer utilizing an activity sensor, and which is incorporated herein by reference.

The activity signal Nact, which is a unitless number, is converted in the practice of this invention to have the same units as QT, i.e. ms, by the following formula:

$$ACT = ACTmpl * Nact$$

By this conversion, Nact can be compared to the QT variable in a combined QT plus ACT algorithm. It is noted that the number of activity senses can be counted in two ways. In a first method, a programmable time is utilized, providing the following formula:

$$Nact = Fact * (\Delta t) = counts,$$

$$ACT = ACTmpl * Fact * \Delta t,$$

where Fact = activity frequency $(S^{-1})$, and $\Delta t$ is the programmable time in seconds.

Alternately, Nact can be counted over predetermined number (N) of intervals, resulting in the following equations:

$$Nact = Fact * N * int/1000$$

where int is in ms; and N is the number of counting intervals;

$$ACT = ACTmpl * (Fact * N * int/1000)$$

In a preferred embodiment, means for obtaining the ACT signal are controlled by a software routine which is entered once every cycle. If the system is programmed to utilize the activity signal, the routine checks to see if Nact is to be read on an interval or time basis. If the moment to read has not arrived, the routine skips out. However, if the moment to read is present, the routine gets the counts (Nact) from the activity sensor and resets the activity counter for the next cycle. Then, optionally, the routine may limit any change in Nact compared to the prior value, if pacing rate is close to URL. Following this, the ACT signal is generated on the basis of the following equations:

$$\text{temp: } (Nact - ACTdr)$$

$$ACT = ACTmpl * \text{temp},$$

where ACTdr is a drift factor, as discussed more fully below.

Figure 5:
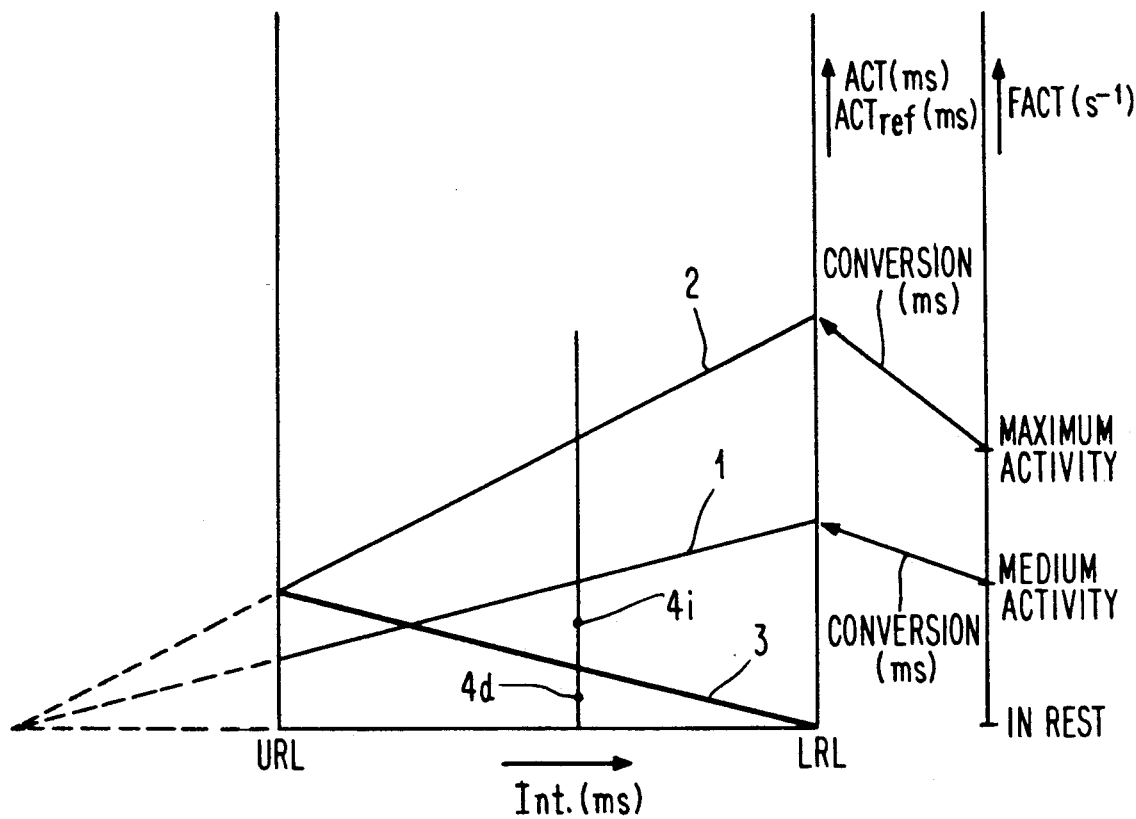
FIG. 5 shows a curve of $ACT_{ref}$ as a function of interval in relation to curves of ACT for different exercise levels.
Figure 6A:
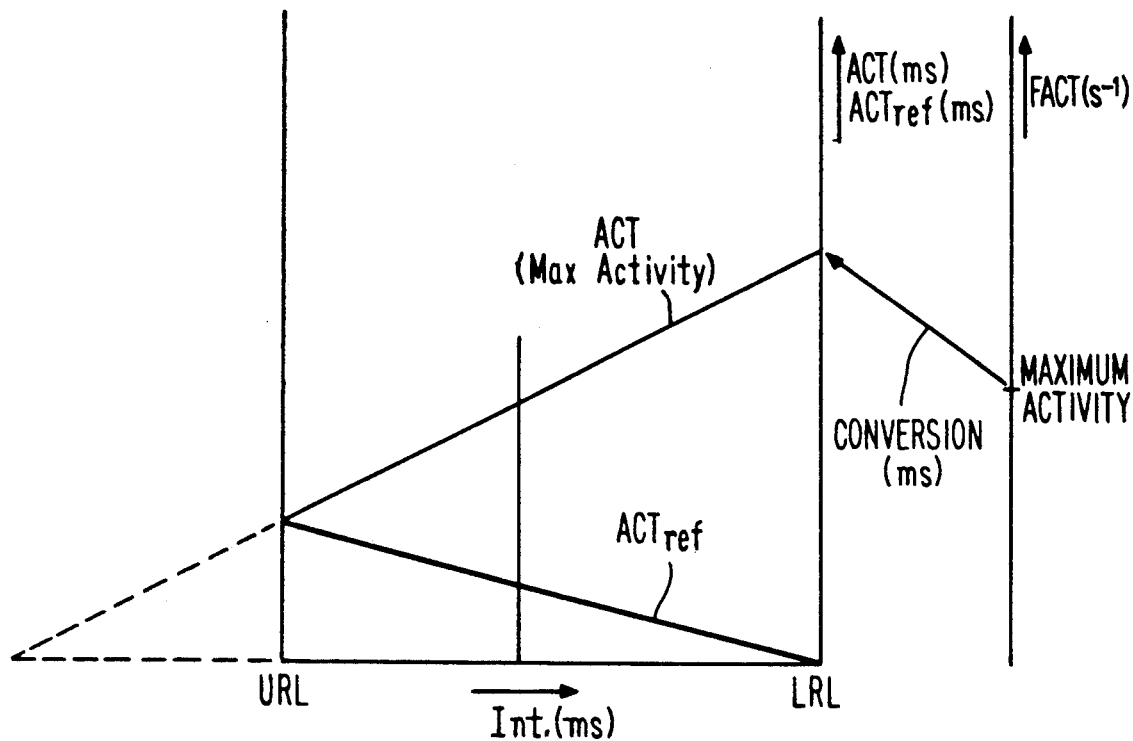
FIGS. 6A and 6B show coupled curves of $QT_{ref}$ and $ACT_{ref}$ as a function of pacing interval, as used in the combination sensor algorithm of this invention.
Figure 6B:
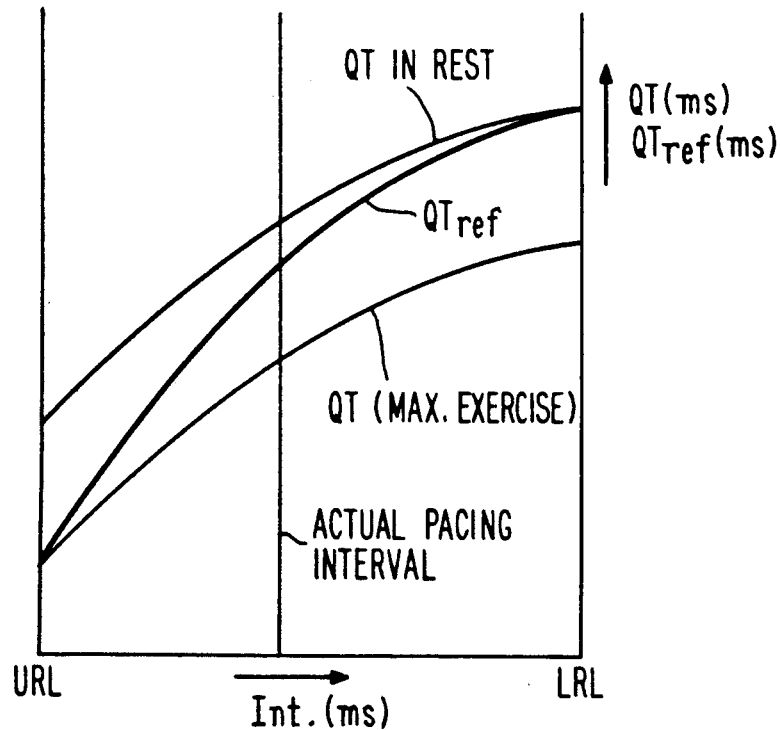

Referring to FIG. 5, there is shown the relation between activity frequency (Fact) and ACT, with ACT presented as a function of interval. Curve (1) represents ACT for medium activity, while curve (2) represents ACT for maximum activity. This figure illustrates how Fact increases as a function of patient activity, and it shows the conversion from Fact to ACT. It is noted also that in this case Nact is counted over N intervals, and that ACT increases as a function of interval (if ACT were determined per a given time period, each ACT line corresponding to a given activity level would be horizontal, and not a function of pacing interval). FIG. 5 also shows the $ACT_{ref}$ curve (3) superimposed on the ACT curves for maximum and medium activity. It is noted that the $ACT_{ref}$ curve must be at zero at LRL, corresponding to no activity when the patient is at rest. The curve must extend to the maximal ACT at URL, corresponding to the highest pacing rate at maximum patient activity. The $ACT_{ref}$ relation is chosen to be linear, according to the following formula:

$$ACT_{ref} = Dact(T_{LRL} - int)$$

FIG. 5 indicates, at point 4i, a situation where the measured activity level at a given interval ($I_o$) is greater than $ACT_{ref}$, indicating that the pacing rate should be incremented; and the situation at point 4d, where the activity level is less than $ACT_{ref}$, indicating that the pacing rate should be decremented. This is summarized as follows:

Point 4i: $ACT > ACT_{ref}$
$ACT_{dif} = ACT_{ref} - ACT < 0$
increment pacing rate Point 4d: $ACT < ACT_{ref}$
$ACT_{dif} = ACT_{ref} - ACT > 0$
decrement pacing rate In the preferred embodiment, as discussed above, there are two coupled reference curves, as shown in FIG. 5. Thus, at the programmable LRL, the QT reference curve correlates minimum stress patient QT at rest and the LRL interval; and the ACT reference curve correlates the minimum patient activity signal at rest and LRL. Likewise, at URL, the QT reference curve correlates patient QT reached at maximum stress and URL, and the ACT reference curve correlates maximum stress ACT and URL. The curves are coupled in the sense that each is designed to indicate approximately the same pacing rate within the LRL-URL range for varying activity or stress levels.

Figure 7A:
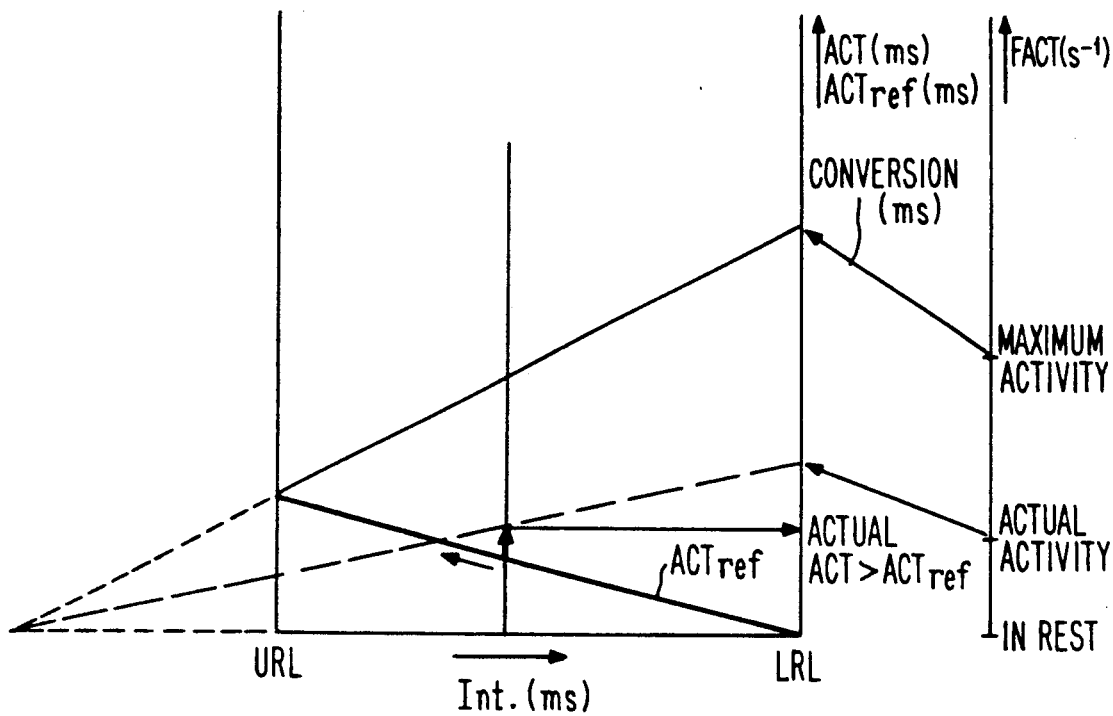
FIGS. 7A and 7B illustrate graphically, with respect to the coupled reference curves, a first situation where both sensor variables indicate an increased rate.
Figure 7B:
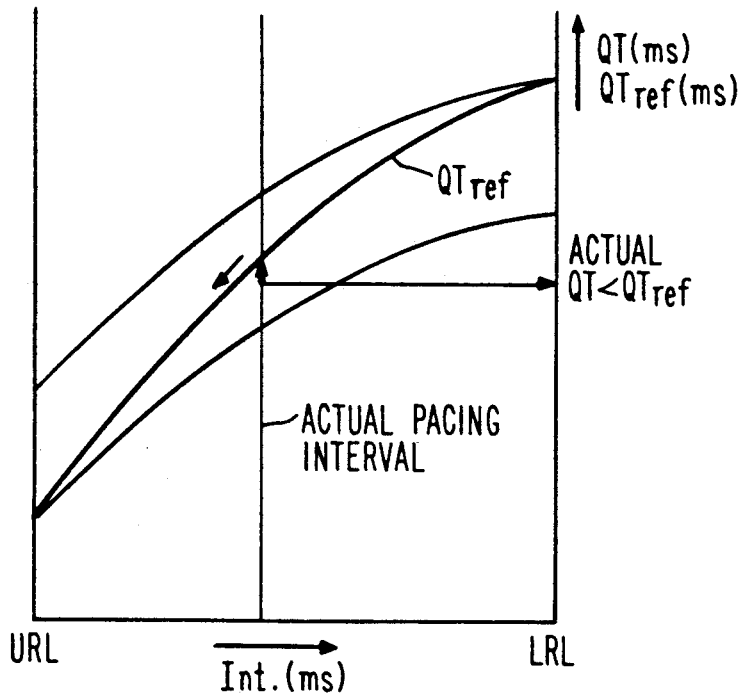
Figure 8A:
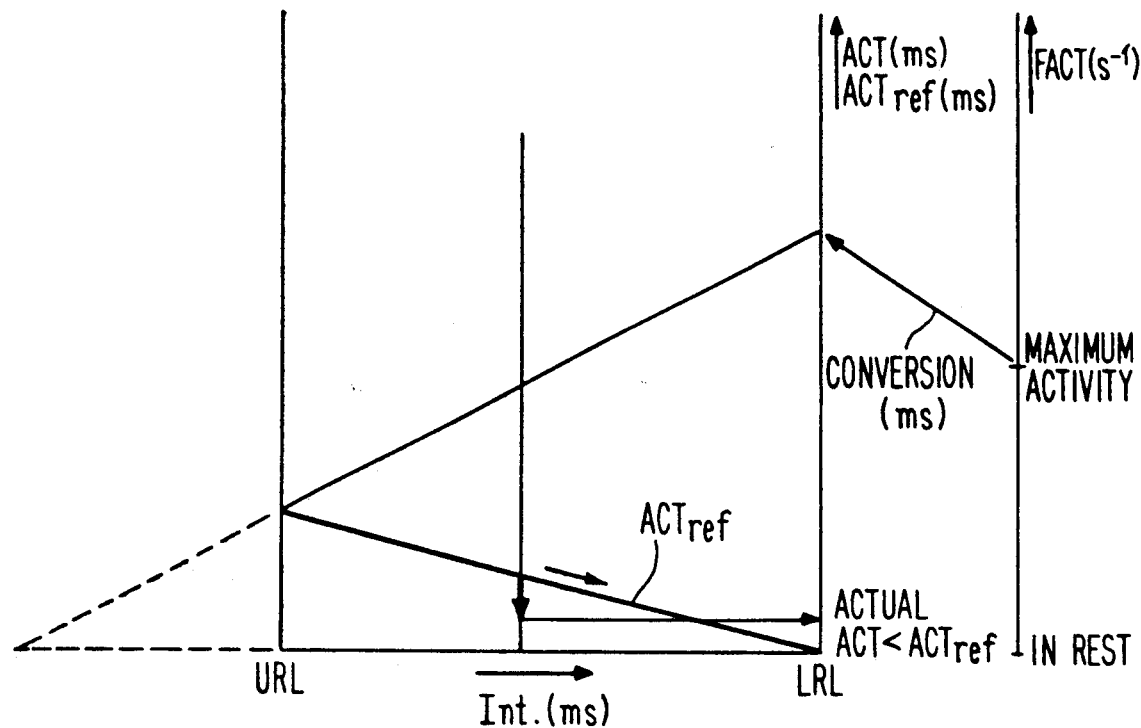
FIGS. 8A and 8B illustrate graphically a second situation where both sensor variables indicate a decreased rate.
Figure 8B:
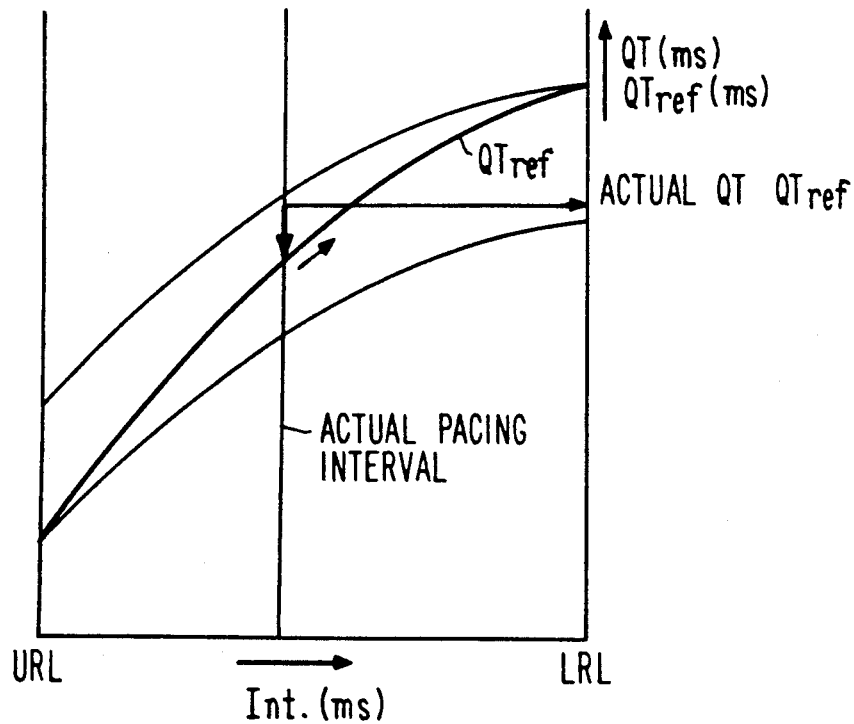
Figure 9A:
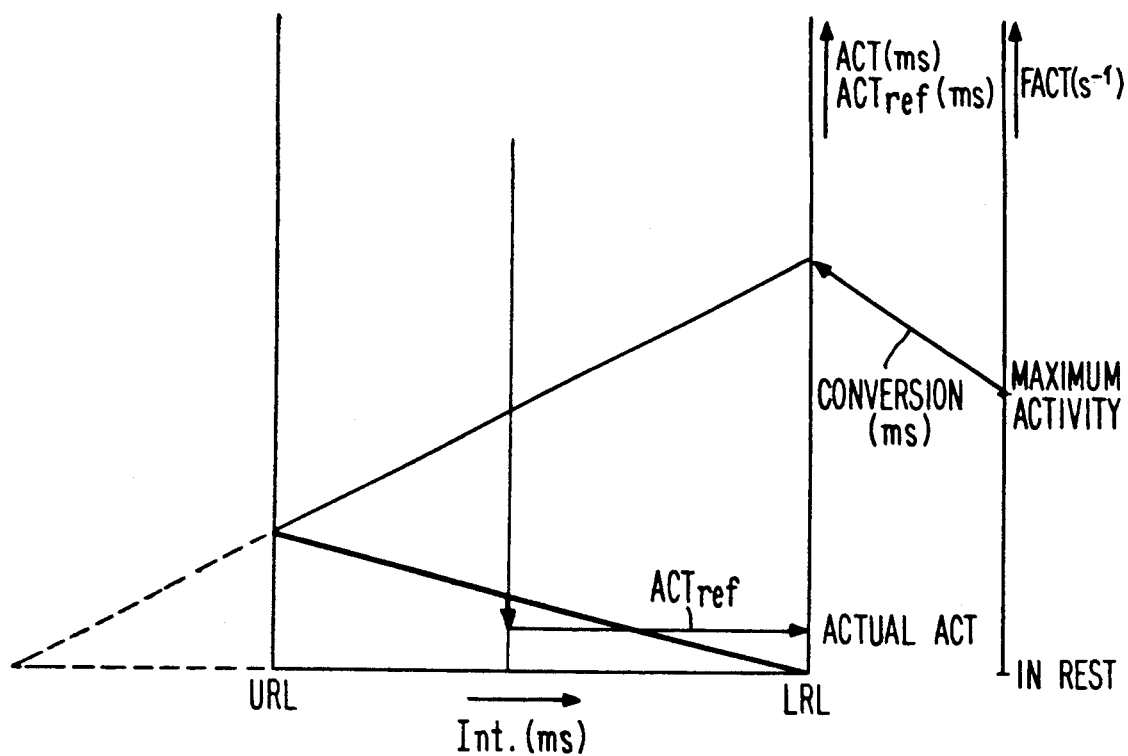
FIGS. 9A and 9B illustrate graphically a third situation where the algorithm indicates an increased rate.
Figure 9B:
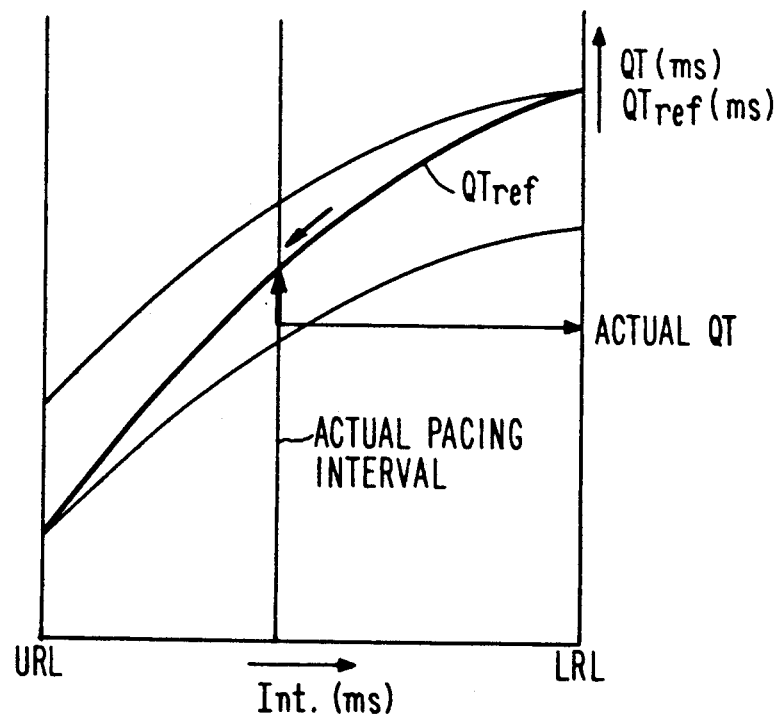
Figure 10A:
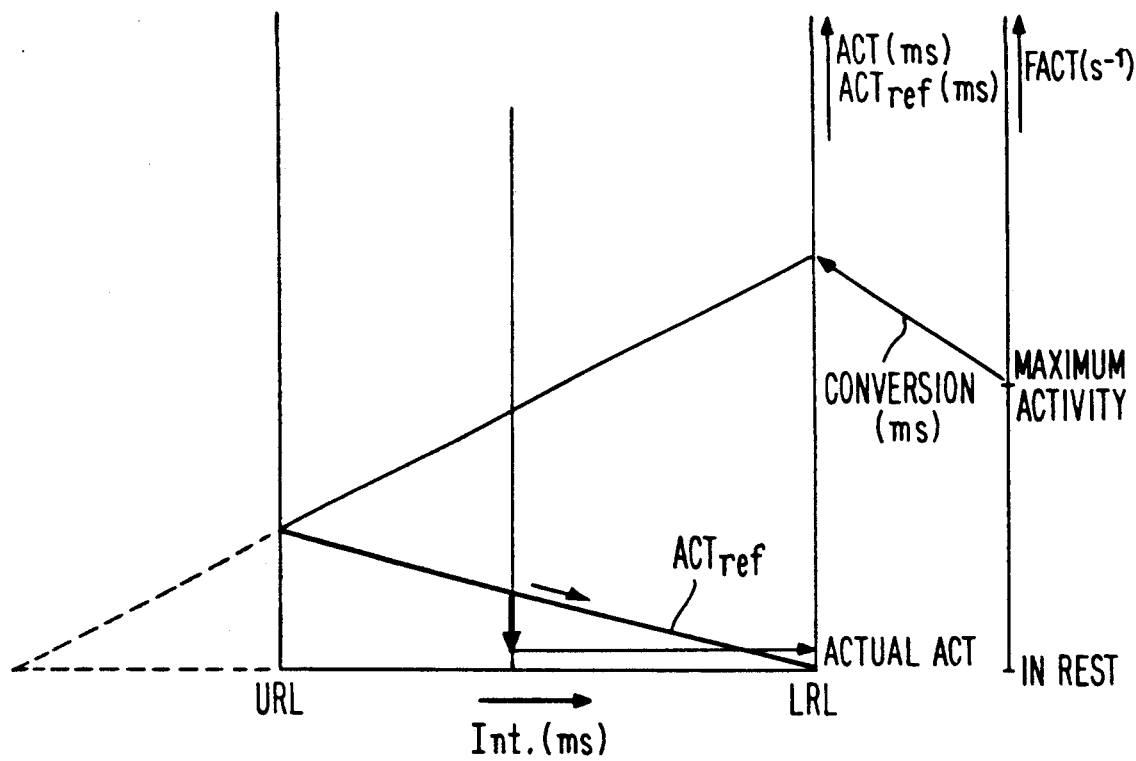
FIGS. 10A and 10B illustrate graphically a fourth situation where the algorithm indicates a decreased rate.
Figure 10B:
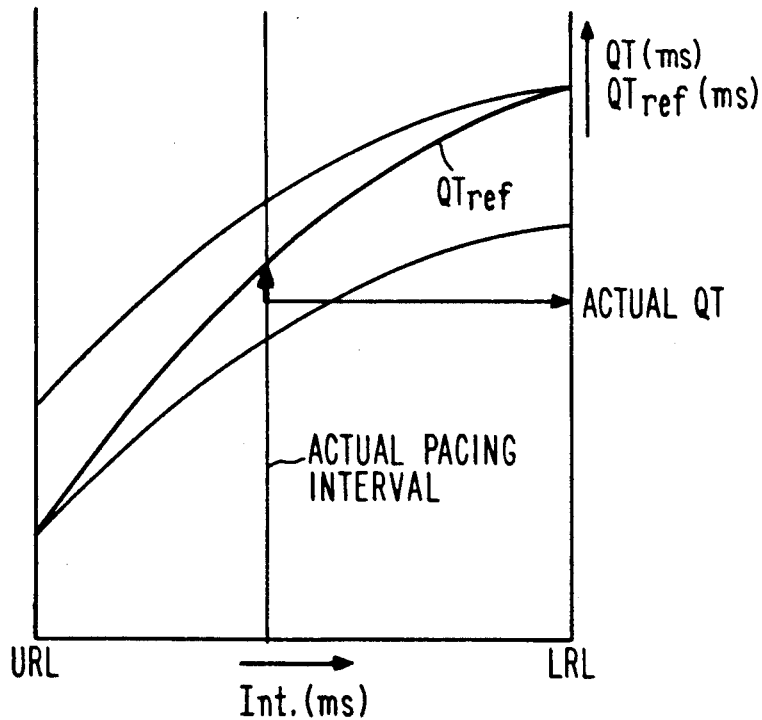
Figure 12A:
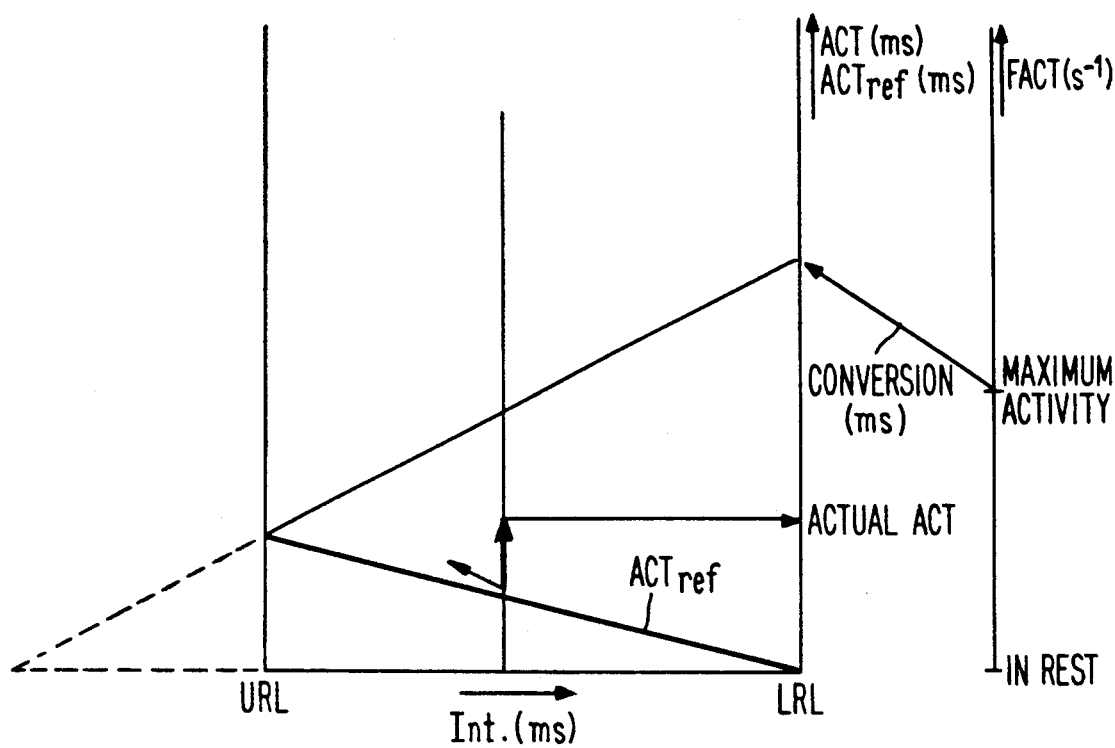
FIGS. 12A and 12B illustrate graphically a sixth situation where the algorithm indicates an increased rate.
Figure 12B:
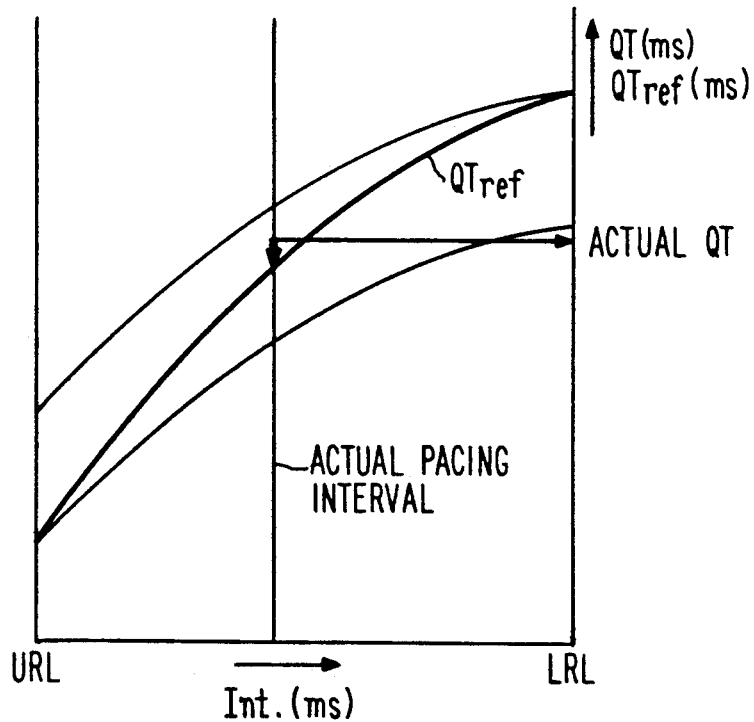

The decision as to whether to increase or decrease pacing rate depends upon comparisons of $QT_{dif}$ and $ACT_{dif}$, as illustrated in FIGS. 7A, 7B-12A, 12B. FIGS. 7A and 7B illustrate the situation where ACT is greater than $ACT_{ref}$ and QT is less than $QT_{ref}$. Note that when QT is less than $QT_{ref}$, a higher rate is indicated; when ACT is greater than $ACT_{ref}$, a higher rate is also indicated. Thus, in this situation, both difference indicators signal an increasing exercise level, calling for an increase in rate. In FIGS. 8A and 8B, ACT is less than $ACT_{ref}$ and QT is greater than $QT_{ref}$. Again, both difference values indicate a decreasing exercise level, so the algorithm prescribes that the rate goes down. In FIGS. 9A and 9B, $ACT_{dif}$ indicates a decremented pacing rate, while $QT_{dif}$ indicates an increased pacing rate. In accordance with this invention, since $QT_{dif}$ is greater than $ACT_{dif}$, the QT influence prevails and the algorithm calls for the rate to go up. In FIGS. 10A and 10B, the situation is the same as in that of FIGS. 9A and 9B, except that $ACT_{dif}$ is greater, and the algorithm responds to prescribe that the rate goes down. In FIGS. 11A and 11B, $ACT_{dif}$ signals increasing exercise, while $QT_{dif}$ signals decreasing exercise. Since the QT influence is the largest, the algorithm calls for the rate to go down. In FIG. 12, the situation is the same as FIG. 11, but since the ACT influence is the largest, the algorithm prescribes that the rate goes up.

As seen from FIGS. 9A, 9B-12A, 12B, the relative influence of the QT and ACT signals are compared by the algorithm to determine, in certain situations, whether the activity parameter or the QT parameter prevails in causing pacing rate to increase or decrease. The relative influence of the activity sensor on the pacemaker response depends upon the comparison between the maximum value of $ACT_{ref}$ at URL, and QT for the highest stress level at URL ($QT_{STR(max)}$). The value for $QT_{STR(max)}$ may not be precisely known for the patient, but generally can be estimated to be approximately 30 ms The maximum value of $ACT_{ref}$ at URL can be set so as to give any fixed relation to $QT_{STR(max)}$. The pacer variable ACTmpl then must be set such that ACTmpl * Nact matches such maximum $ACT_{ref}$ at URL. Note that ACTmpl determines the ACT signal, so if ACTmpl is small, this minimizes the influence of ACT. Likewise Dact, which represents the linear variation of $ACT_{ref}$ with interval, establishes desired variations of pacing rate with change in activity level, and if Dact is small, this also minimizes the influence of ACT. On the other hand, if both Dact and ACTmpl are relatively large, then ACT has a relatively greater influence on the decision made by the algorithm to increase or decrease pacing rate.

Figure 13A:
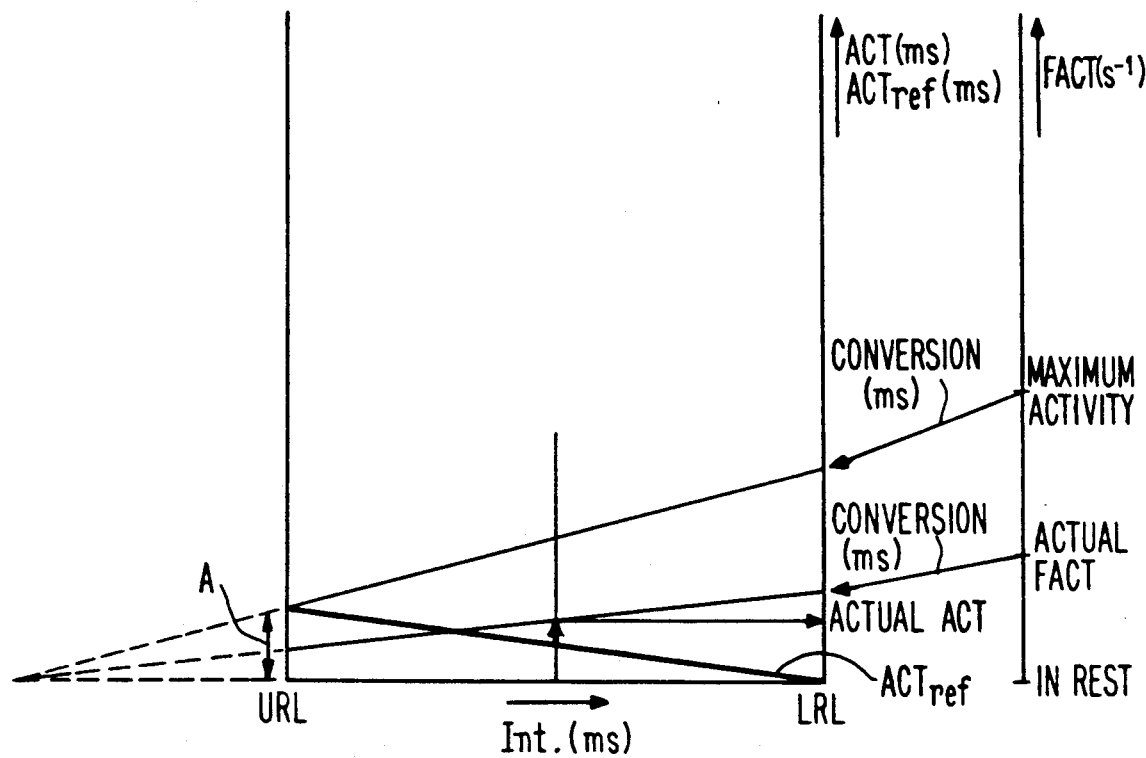
FIGS. 13A and 13B illustrate graphically a situation where the ACT variable has a lesser influence than the QT variable.
Figure 13B:
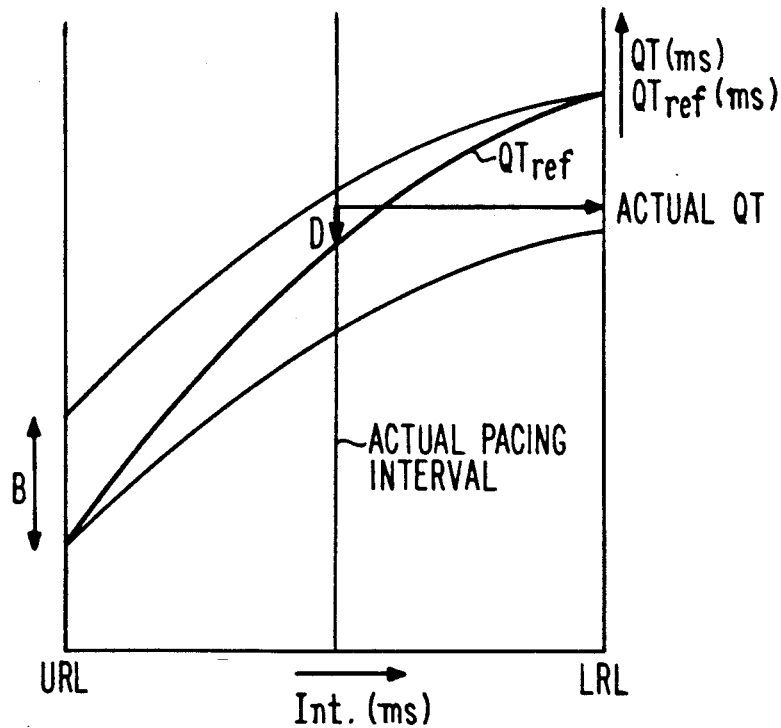
Figure 14A:
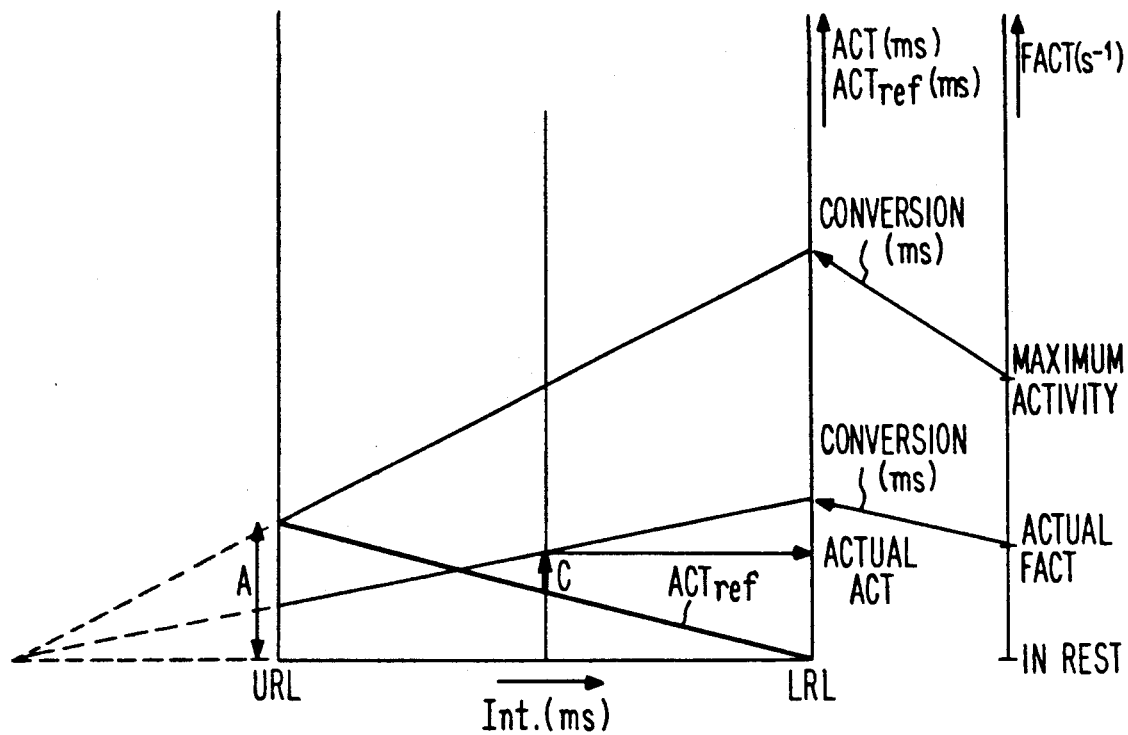
FIGS. 14A and 14B illustrate graphically a situation where ACT and QT have about the same influence.
Figure 14B:
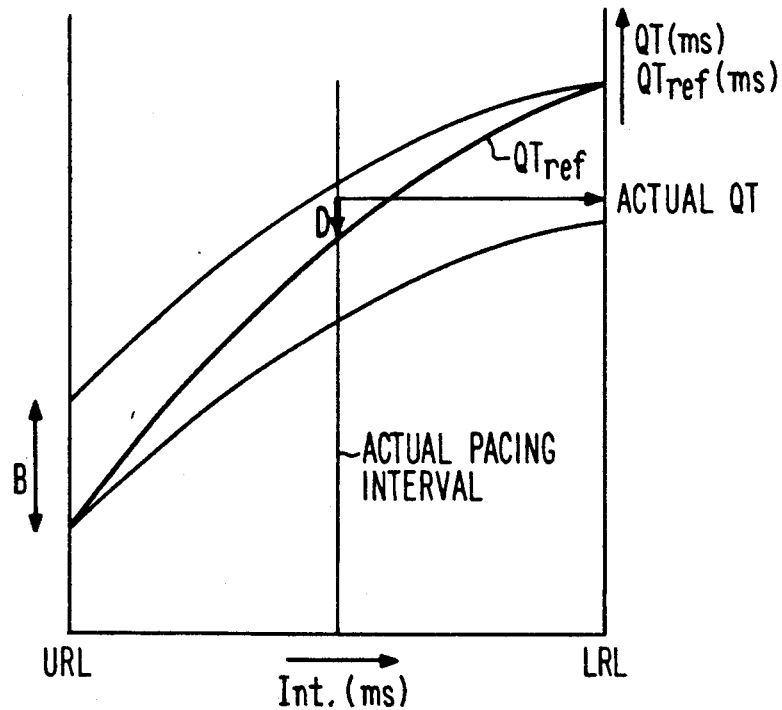
Figure 15A:
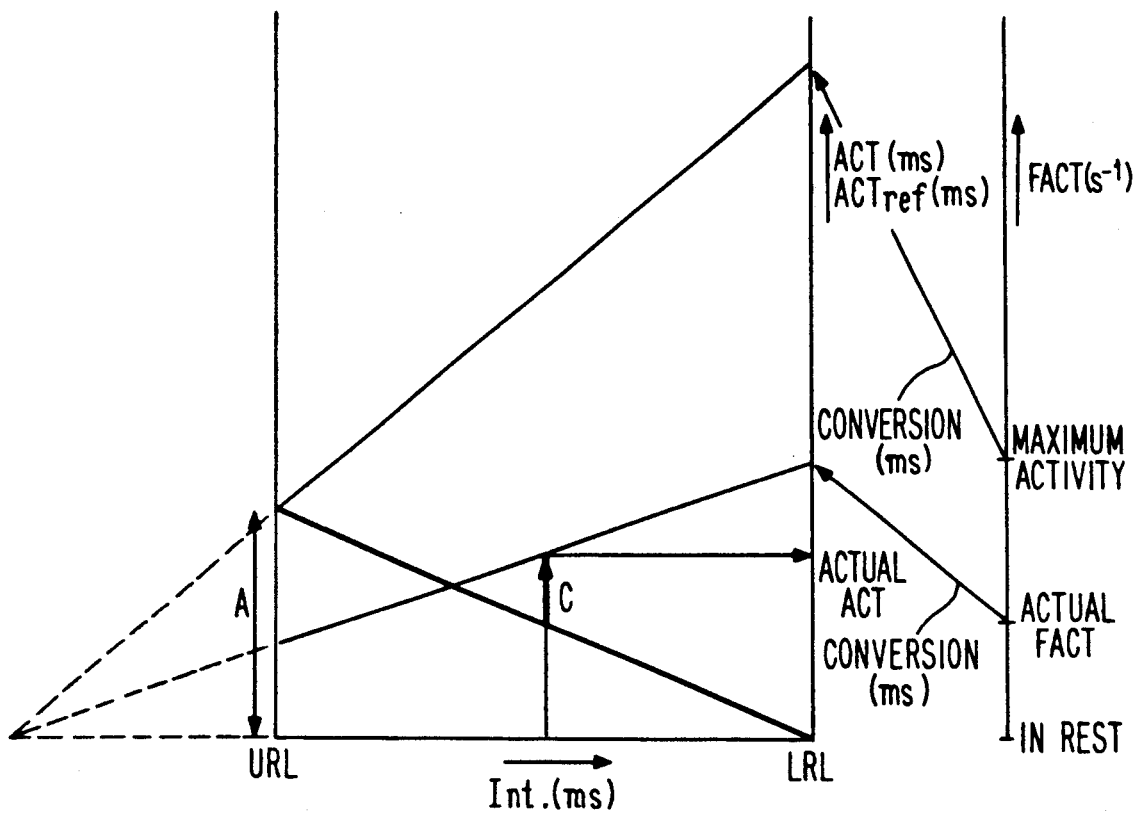
FIGS 15A and 15B illustrate graphically a situation where ACT has a greater influence than QT.
Figure 15B:
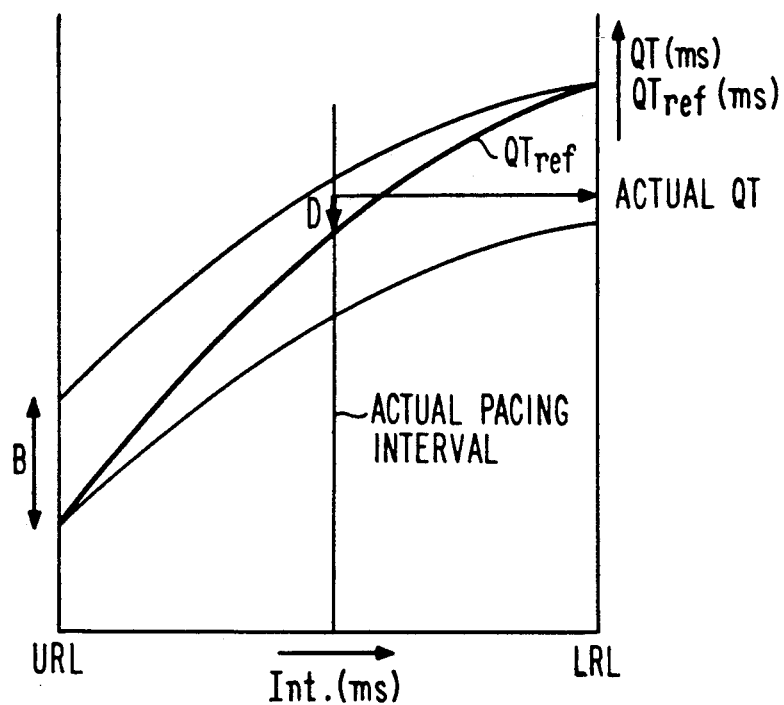

Referring to FIGS. 13A, 13B, 14A, 14B, and 15A, 15B, there are represented three situations which illustrate the relative influence between QT and ACT. In all three figures, ACT indicates an increasing exercise level, whereas QT indicates a decreasing exercise level. In the situation of FIG. 13A, 13B, ACTmpl and Dact are small (A<B), so ACT has little influence (C<D). Since QT has the greater influence, the rate is caused to go down. In FIG. 14A, 14B ACTmpl and Dact are chosen such that ACT and QT have substantially equal influence (A=B), and the algorithm will maintain pacing rate the same (except that each single step it will increment or decrement). In the situation of FIG. 15A, 15B, ACTmpl and Dact are relatively large (A>B), causing ACT to have greater influence (C>D). This results in the algorithm causing the rate to increase.

Figure 16:
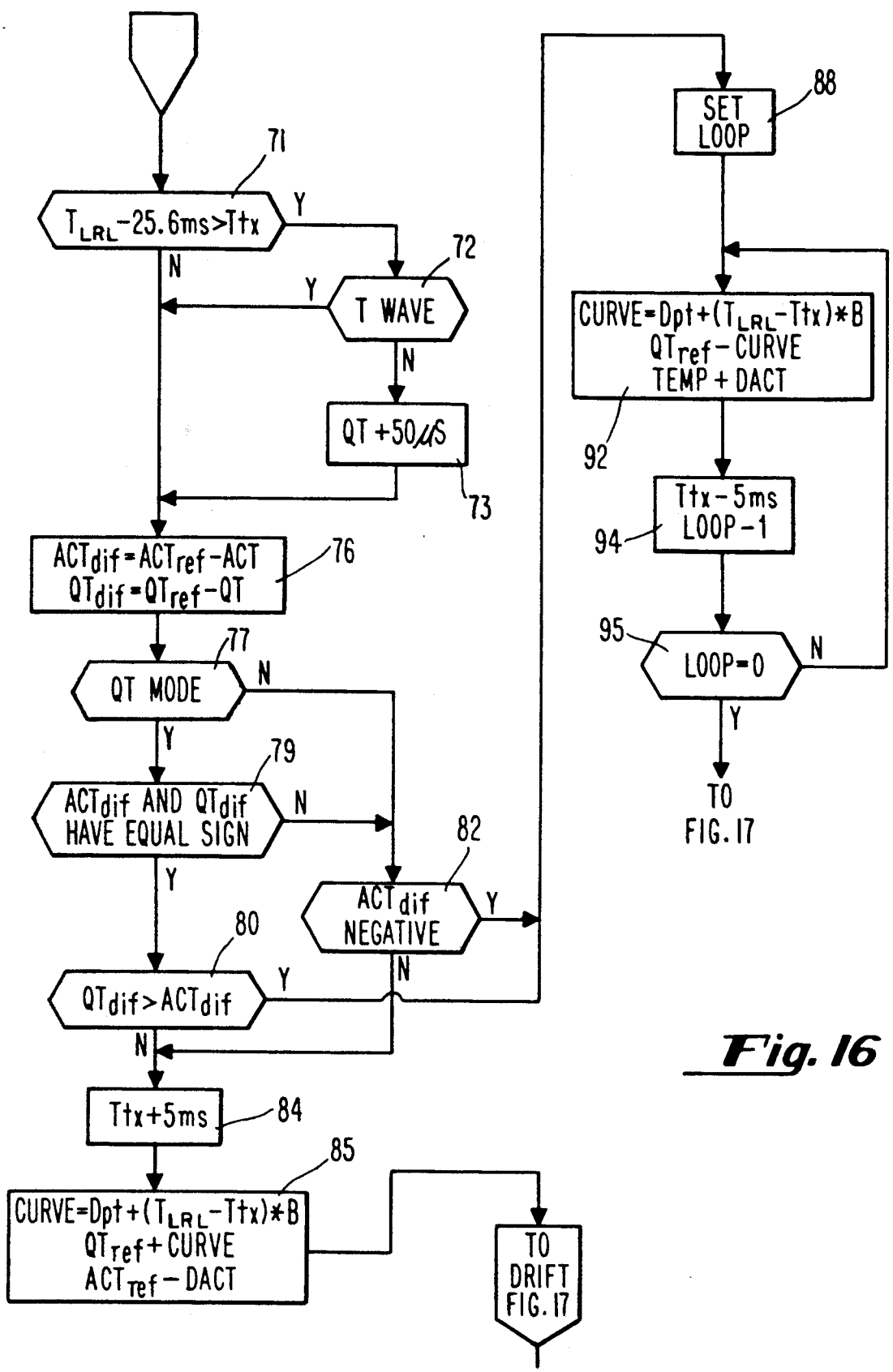
FIG. 16 is a flow diagram of the portion of the preferred algorithm of this invention for changing pacing rate as a function of sensed QT and activity signals.

Referring now to FIG. 16, there is shown a flow diagram of a preferred rate algorithm incorporating both the QT and activity (ACT) variables. The steps of this specific algorithm are carried out each cycle following delivery of a pacing stimulus. Reference is also made to FIGS. 7-15 which illustrate the effect of the algorithm under varying situations.

As indicated at 71, it is first determined whether the pacing rate is near LRL. This is done by comparing the measured time interval (Ttx) to the value of the interval corresponding to LRL ($T_{LRL}$) minus 25.6 ms. If Ttx is smaller than this interval, meaning that it is not within 25.6 ms of lower rate limit interval, then the program branches to block 72 where it is determined whether the T wave has been sensed. If yes, or if the actual pacing interval is within 25.6 ms of $T_{LRL}$, the program branches to block 76. If no T wave has been sensed, such that QT rate information is not available, the program branches to block 73 where the last measured QT value is increased by an arbitrary amount, e.g. 50 μs. Thus, the pacer provides a drift to the QT value which causes it to increase toward $T_{LRL}$ when no T waves are sensed. However, when the pacing rate comes near to LRL, the drift in QT stops. In practice, the drift of QT is limited to a predetermined value, since a high activity level sensed by the activity sensor could maintain the pacer far from LRL, in which case a prolonged period of absence of T wave sensing would cause the variable QT otherwise to drift lower than a value corresponding to $T_{LRL}$.

Following the decision as to whether to cause QT to drift, the software makes a decision as to whether to increment or decrement the rate, in accordance with the steps carried out at blocks 76, 77, 79, 80 and 82. As indicated at block 76, the difference variables, $ACT_{dif}$ and $QT_{dif}$ (as defined above), are determined by subtracting the ACT and QT values from their respective corresponding reference values at the current interval, Ttx. As per the above discussion, an increase in the ACT variable so that it has a higher value than the $ACT_{ref}$ variable is an indication of increase of rate, such that a negative $ACT_{dif}$ indicates a desired rate increase, and vice versa. At the same time, a decrease in sensed QT value to the point that it is less than $QT_{ref}$, causing a positive $QT_{dif}$, indicates a rate increase, and vice versa. Thus, while the difference variables are comparable in the sense that ACT is treated as a substitute parameter to QT, the difference in sign needs to be taken into account. At block 77, the pacemaker determines whether it is in the QT mode, i.e. whether the QT parameter is being utilized. If no, the program branches to block 82 where further logic is based on the activity signal alone. If yes, the program goes to block 79 where the signs (plus or minus) of $ACT_{dif}$ and $QT_{dif}$ are compared. If these signs are found not to be equal, in other words unequal, the program branches to block 82. In such case, both variables point to the same direction of change (FIGS. 7 and 8), and at 82 $ACT_{dif}$ is utilized to determine whether the rate should be increased or decreased. If $ACT_{dif}$ is negative, then an increase in rate is indicated, and the program branches to block 88. If $ACT_{dif}$ is not negative, then a decrease in rate is indicated, and the program branches to block 84. Note, as discussed above, there can be two situations where the difference values have equal signs, namely where QT is less than $QT_{ref}$ and ACT is greater than $ACT_{ref}$; and where QT is greater than $QT_{ref}$ and ACT is less than $ACT_{ref}$. However, if at 79, the difference variables have unequal signs, which happens in four situations, the program branches to block 80. There it is determined which parameter has the greatest influence, by determining whether $QT_{dif}$ is greater than $ACT_{dif}$. If yes, an increase in rate is called for, and the program branches to block 88. If no, a decrease in rate is called for, and the program branches to block 84.

At block 84, the current interval Ttx is increased by 5 ms, i.e. the pacing interval is increased by 5 ms Then, at block 85, new points on the QT reference curve and ACT reference curve are calculated, to correspond to the new interval. The new $QT_{ref}$ is calculated by increasing $QT_{ref}$ by an incremental amount "curve" calculated as follows:

$$Curve = Dpt + B (TLRL - Ttx)$$

At the same time, a new point on the activity reference curve is calculated by decreasing $ACT_{ref}$ with the value Dact. $ACT_{ref}$ cannot be decreased below a predetermined minimum. Thus, the decision to decrease rate results in increasing the interval by 5 ms, and adjusting the reference points on the reference curves of both $QT_{ref}$ and $ACT_{ref}$.

If the comparisons made at blocks 79 and 80 indicate an increase in rate, the program proceeds to block 88 where a calculation of step size is made. The interval change during increase of rate is made dependent upon the interval, i.e., Ttx. This feature limits change of pacing rate at very high rates (corresponding to short intervals) and permits larger pacing interval changes with increasing intervals. For the preferred embodiment, the correspondence between interval and step size is set forth in the following table:

| Interval | Stepsize |
| --- | --- |
| <614.4 ms | 5 ms = 1 * 5 ms |
| 614.4–819 ms | 10 ms = 2 * 5 ms |
| 819.2–1024.0 ms | 15 ms = 3 * 5 ms |
| >1024.0 ms | 20 ms = 4 * 5 ms |

A computer value "LOOP" is set to N=1, 2, 3 or 4 depending upon the selected step size. Following determination of step size, the software goes into a loop comprising blocks 92, 94 and 95. At 92, a new value of $QT_{ref}$ is determined. $QT_{ref}$ is decremented by the amount indicated as "curve", being the same amount set forth below with respect to block 85. A computer value "temp" is determined, which is used to increment $ACT_{ref}$ if URL has not been reached (as discussed below in connection with block 102). Temp, which is initialized at zero when the LOOP value is set, is incremented by the constant Dact. Next, at block 94, the pacing interval is decremented by 5 ms. The variable LOOP is decremented by one, and then at 95 it is determined whether LOOP is zero. If no, the software loops through blocks 92 and 94 again, until LOOP variable is zero, at which time it exits. Thus, for every step decrease in interval a corresponding step in $QT_{ref}$ and $ACT_{ref}$ is calculated, to adjust the reference curves. Thus, $QT_{ref}$ is decremented and $ACT_{ref}$ is incremented in the loop a number of times corresponding to the calculation of step size at block 88.

Figure 17:
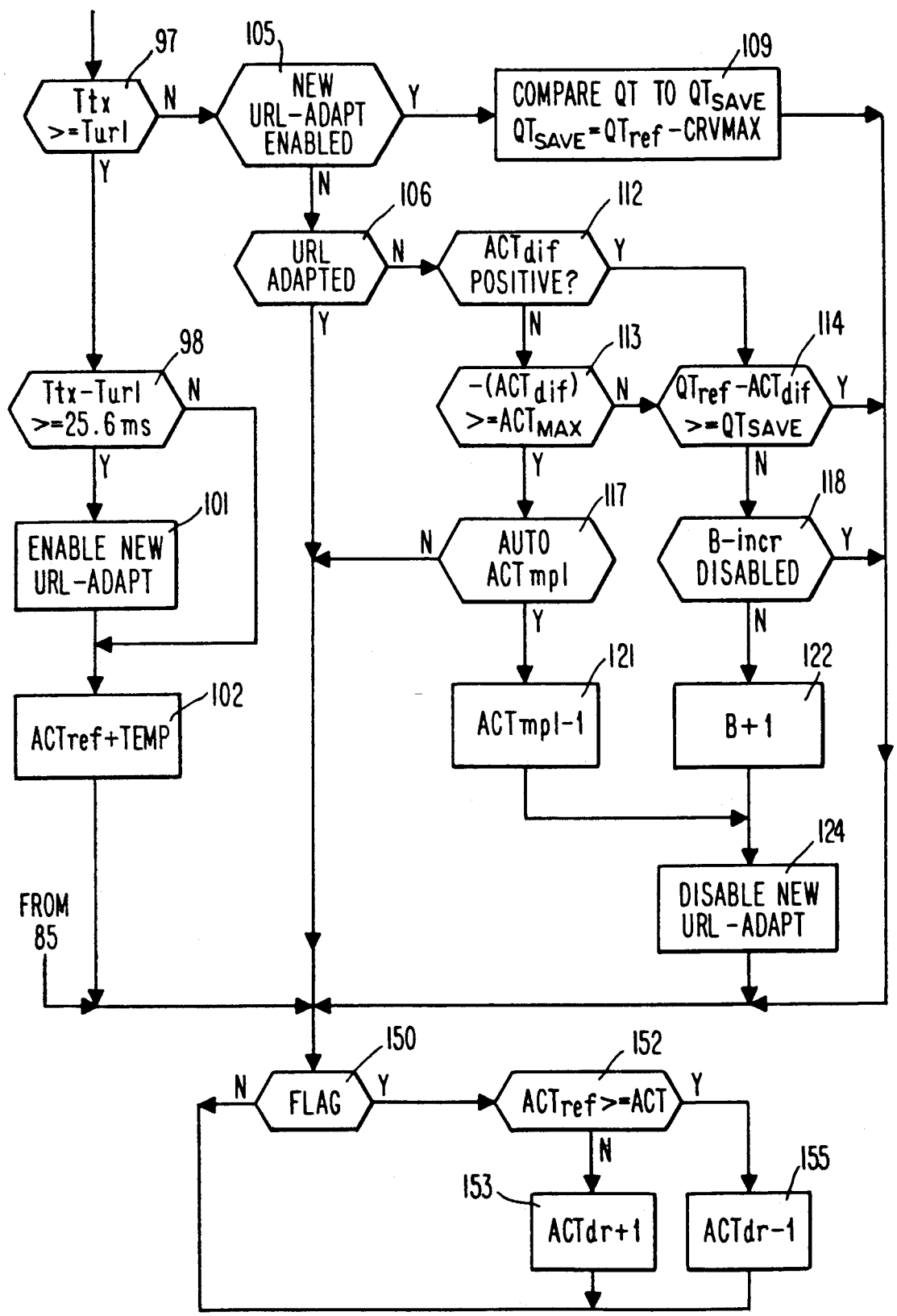
FIG. 17 is a flow diagram of the portion of the preferred algorithm of this invention for adjusting operation of the pacer at URL, and of a portion of the algorithm of the preferred embodiment of this invention for setting the activity drift ($ACT_{dr}$) factor under predetermined conditions.

Referring now to FIG. 17, there is illustrated a portion of the algorithm for adjusting operation at URL. The $QT_{ref}$ curve at URL is controlled by the factor B, such that QT response at URL can be adjusted by changing the value of B. The algorithm of this invention utilizes the logic that if QT shortens more than a programmable threshold (pacer variable CRVMAX) after pacing rate reaches URL, then URL was reached too quickly for the patient. Thus, the condition is met if $$QT < QTsave,$$

where $QTsave = QT_{ref} - CRVMAX$.

The $QT_{ref}$ curve is adjusted by incrementing B, which effectively lowers the value of $QT_{ref}$ at URL. B is incremented if:

1) the pacing rate has reached URL;
2) after reaching URL, QT shortens additionally by at least an amount equal to CRVMAX; and
3) $QT_{ref} - ACTdif < QTsave$.

Note that if the third condition is not met, then decrementing the value of B would mean that the pacemaker could not reach a stable point on the reference curves where $QT_{ref} - QT = ACT_{ref} - ACT$.

The activity response may also be adjusted as a function of conditions at URL. Note that ACTmpl * Nact must match the maximum $ACT_{ref}$ value at URL. Since the coefficient Dact is programmed and cannot be automatically changed, ACTmpl is decremented one step whenever the pacer reaches URL and ACT exceeds the programmable variable ACTmax. Whenever ACT mpl has been decremented, it will automatically be incremented once later, e.g., after 8 days.

Still referring to FIG. 17, following an increase of the rate (decrementing interval), the software goes from block 95 (FIG. 16) to 97, where it is determined whether pacing rate has reached URL. Thus, if Ttx is smaller than TURL, upper rate limit has been reached and the program branches to 105. If no, upper rate limit has not been reached and the program branches to block 98. At block 98 it is determined whether the pacing rate has come within 25.6 ms of upper rate limit. If yes, at block 101, a "new URL adapt" is enabled. Since Ttx is less than $T_{URL}$, ACT ref is adjusted by adding "temp" as calculated at block 92.

Returning to block 105, if URL has just been reached, and new URL adapt is enabled, the program branches to block 109. At this point QT is compared to QTsave, as defined above. If QT is less than QTsave, a software save register is set so that during the next cycle at 105 the answer is no, and the program exits. In the next cycle, at 105 the program branches to block 106. If URL has already been adapted, the program exits; if not, it branches to 112 where it is determined whether $ACT_{dif}$ is positive. If yes, the program branches to block 114. There the difference between $QT_{ref}$ and $ACT_{dif}$ is compared to QTsave. If this difference is positive, the program exits. If this difference is less than QTsave, it means that $ACT_{dif}$ is greater in magnitude than the increment CRVMAX, such that $QT_{ref}$ at URL can be decremented. The program then proceeds to 118 to determine whether the B variable can be incremented. If it can, at 122 B is incremented, and then at 124 the new URL adapt flag is disabled. Returning to block 112, if $ACT_{dif}$ is not positive, at 113 the algorithm determines whether the negative of $ACT_{dif}$ is greater than the maximum value of ACT. If no, then B can be incremented and the program branches to 114. If yes, it means that the 5 NACT counts exceed a predetermined value and the program goes to 117 where it is determined whether automatic decrementing of ACTmpl is enabled. If yes, at block 121, ACTmpl is decremented, and the program branches through to 124.

The pacemaker of this invention also provides for automatic adjustment of rate response at LRL, as set forth in U.S. Pat. No. 4,972,834. When the patient is at rest (and the pacing rate is near LRL, the pacemaker paces for a while at LRL and calculates an average QT at LRL. The pacemaker then decreases the pacing interval by a small amount and calculates a second QT average at the second interval, near LRL. The difference in two QT averages and the difference in the two intervals are divided to provide the coefficient corresponding to pacer variable Dpt. This is compared to the prior value of the coefficient, and the value of Dpt is then adjusted one step in the direction of the indicated change. Thus, if the ratio indicates a greater slope at LRL than had 2.5 previously represented by the value of Dpt, Dpt is increased so that the $QT_{ref}$ curve near LRL is steeper. By this technique, after a number of such slope measurements the $QT_{ref}$ curve near LRL is adapted to substantially match the QT curve of the patient's heart.

Referring now to FIGS. 17, 18A, 18B, 19A, and 19B, there is illustrated the drift action incorporated in the preferred embodiment, for adjusting the ACT parameter in situations where the activity signal does not correlate with QT. It is known that the activity sensor is not always a proportional indicator, and excessively high activity level may be indicated in several situations. For example, if the patient is in rest and yet activity signals are counted, e.g., caused by respiration or the patient's heartbeat, the activity indication is too high and should be decremented. Likewise, there are situations where Nact may be too high to correspond to the actual exercise level, such as where vibrations are sensed which are caused by external forces. To account for these influences, and decrease the ACT signal accordingly, ACT is periodically compared to $ACT_{ref}$ as seen in block 150. Since the $QT_{ref}$ curve and the $ACT_{ref}$ curve are coupled so that movements along the $QT_{ref}$ curve should be matched with movements along the $ACT_{ref}$ curve, if ACT does not match $ACT_{ref}$, this is an indication that the sensed activity signal is incorrect. By causing the ACT signal to drift in such a situation, i.e., by adjusting it to decrease the magnitude of $ACT_{dif}$, the activity information is correlated with the QT information. To accomplish this, ACT is adjusted by a drift signal, referred to as ACTdr, according to the following formula:

$$ACT = ACTmpl * (Nact - ACTdr)$$

Figure 18A:
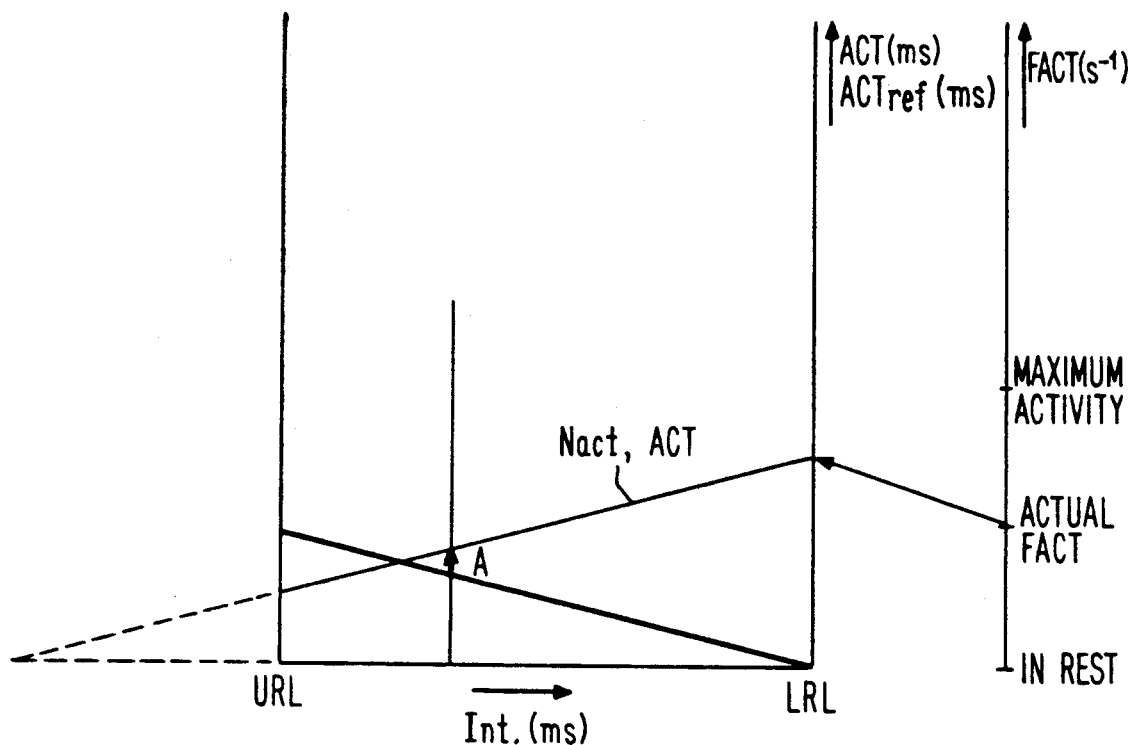
FIGS. 18A and 18B illustrate graphically a situation where the algorithm indicates start of ACT drift, causing ACT to decrease.
Figure 18B:
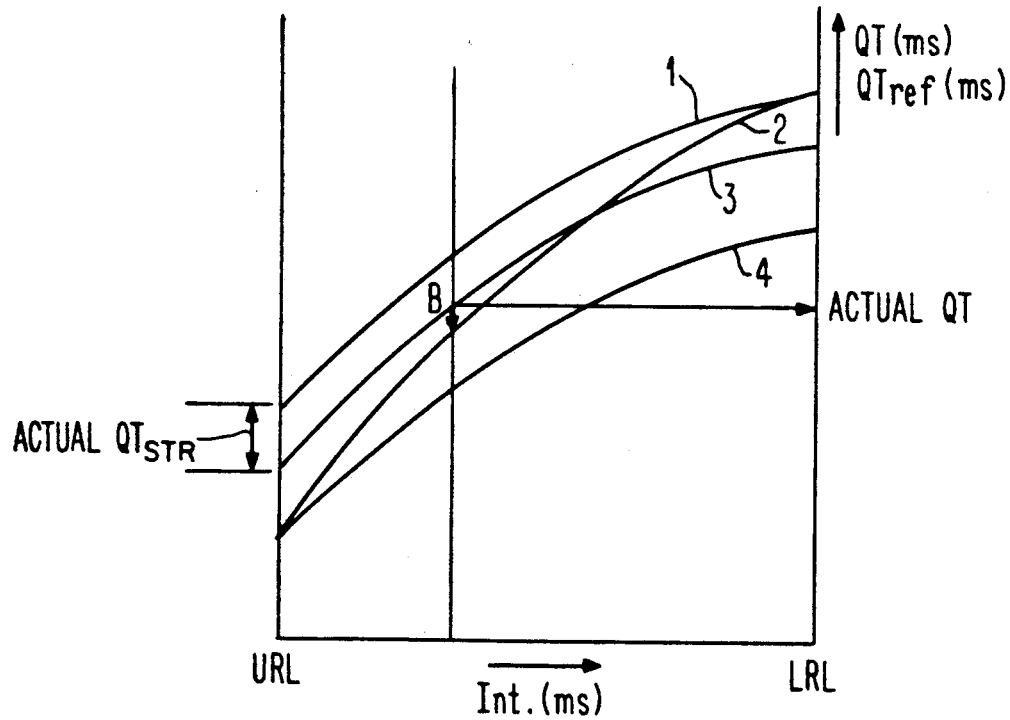
Figure 19A:
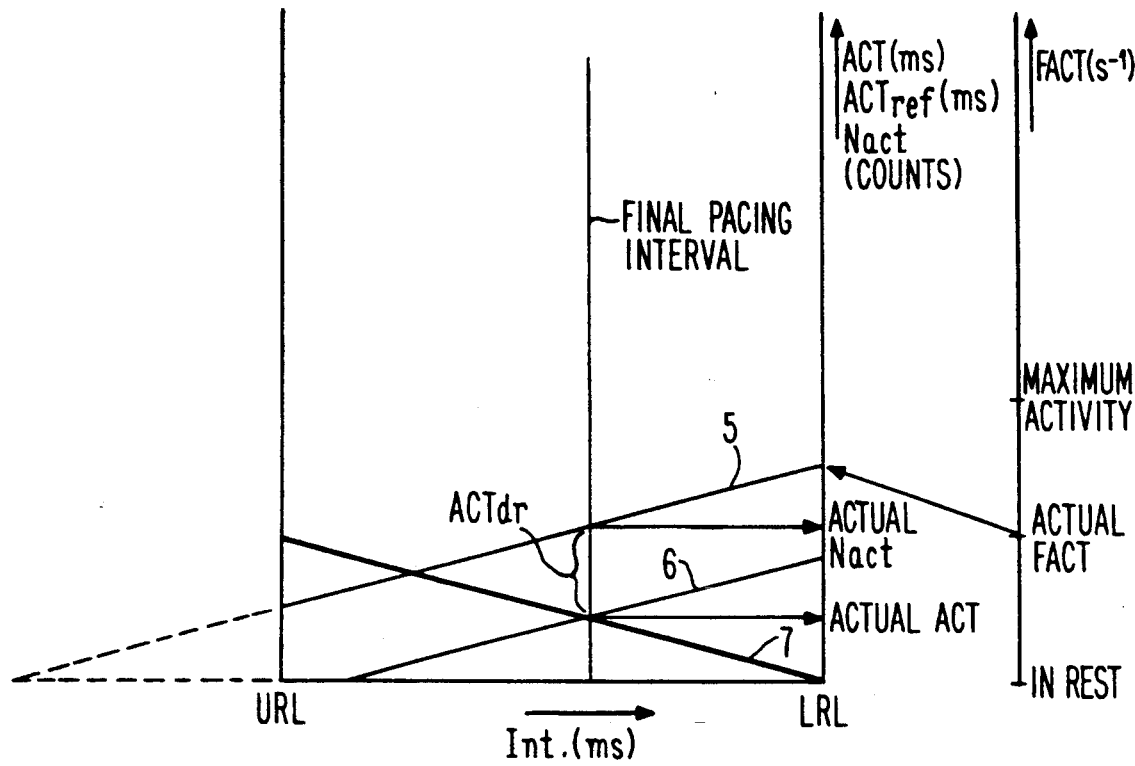
FIGS. 19A and 19B illustrate graphically the situation sometime following that of FIGS. 18A and 18B, where rate has decreased and ACT drift has increased to the stable condition where $ACT = ACT_{ref}$ and $QT = QT_{ref}$.
Figure 19B:
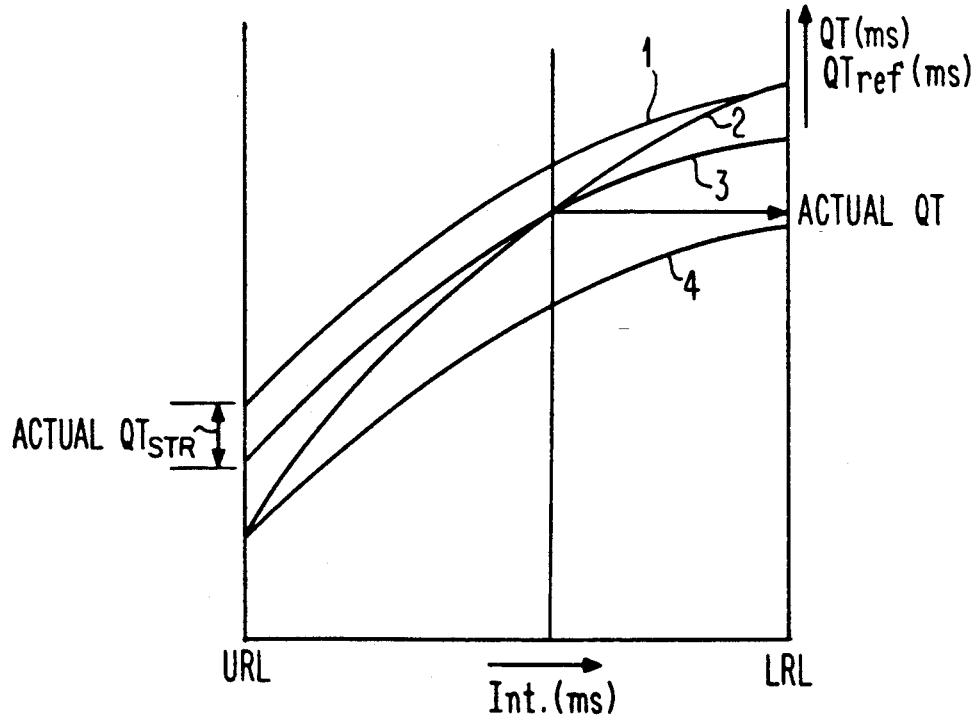

As can be seen, the drift factor, ACTdr, essentially compensates for any inaccuracy in the sensed Nact variable. If ACT is measured to be larger than $ACT_{ref}$, ACTdr is increased, thereby causing ACT to decrease, bringing it back into correlation with QT. At block 152 of FIG. 17, if $ACT_{ref}$ is found not to be greater than ACT, the program branches to block 153, where ACTdr is incremented by one unit, which results in a decreased value of ACT. The algorithm checks at block 153 to set an upper limit on the value of ACTdr. If the comparison at 152 is such that ACT is less than $ACT_{ref}$, then the program branches to block 155, and decrements ACTdr. A limit is placed on ACTdr such that it cannot go below zero. In this embodiment drift compensates only for false positives: a rate indication by the activity sensor which is high compared with the QT information. Thus, the algorithm periodically introduces the drift factor compensation into the ACT signal, thereby either increasing or decreasing the ACT signal. This is illustrated in FIGS. 18A, 18B, 19A and 19B for the situation where ACT is greater than $ACT_{ref}$. As indicated in FIG. 18B, the QT signal is greater than $QT_{ref}$, indicating that the pacing rate should go down, i.e., interval should increase. However, ACT is greater than $ACT_{ref}$, and ACTdr is incremented. When the pacemaker stabilizes to a final situation, as shown in FIGS. 19A, 19B, ACTdr has been incremented so that the actual ACT has come to equal $ACT_{ref}$. In FIGS. 19A, 19B, for the increased pacing interval, the ACT curve with drift is shown at curve 6, being displaced downwardly from curve 5 without drift (which corresponds to actual Nact). Note also that the position on the $QT_{ref}$ curve has changed so that it corresponds to a lower actual stress, and QT equals $QT_{ref}$. In the reverse situation where ACT is less than $ACT_{ref}$, ACTdr would be decremented to bring the ACT signal back into correlation with the QT signal, limited by the fact that only positive $ACT_{dr}$ values are allowed.

The embodiment as illustrated permits drift to correct only for a false positive, i.e., the situation where the second sensor value (ACT) gives too high an indication compared to the first sensor value (QT). However, the algorithm can be adapted to apply drift for a false negative, e.g., by decrementing $ACT_{dr}$ to a negative value. Also, it is to be understood that the drift feature may be programmed to compensate the fast sensor by other than fixed steps in order to reduce the fast sensor influence to or toward zero over time.

As discussed above, the system and method of this invention is applicable to employing two or more control parameters. It is noted that hardware simplification of the system can be achieved if a second or extra control parameter can be obtained without the need of an extra sensor means. This can be achieved in a system where QT is a primary parameter, by utilizing another parameter obtained by the sensed heartbeat signal. For example, the amplitude of the T wave (TwA) can be utilized as a control parameter separate from QT, as can other features of the Q or T wave portions of the sensed heartbeat signal. See U.S. Pat. No. 4,305,396. The parameter TwA has a reasonably quick response, i.e., reacts to changing patient conditions more quickly than does the QT interval. Thus, TwA is a good choice of a second parameter to be used in combination with QT. In accordance with this invention, the amplitude of the T wave can be determined each cycle by signal processing circuitry such as illustrated at block 58 of FIG. 1. Data for a TwA reference curve may be programmed into the pacing system to provide a coupled reference curve, as well as conversion data for converting the amplitude signal into a comparable signal with units of ms. Such a system has the advantage of needing no extra sensor, since both control parameters are obtained from the same pacing lead 53 as is conventionally used for introducing stimulus pulses into the ventricle. Alternately, the TwA or any other control parameter derived from the sensed heartbeat signal may be utilized as a third control parameter. Of course, while the preferred embodiment of this invention has been illustrated as using QT as a primary control parameter, it is to be understood that any other sensor signal could be the primary control parameter, and the secondary parameter would be converted into the units of the first parameter. This invention embraces control parameters such as AR interval, R wave morphology, T wave morphology, impedance changes, and other variables including those set out above under the Description of the Background, in any combination of two or more.

While the invention has been illustrated by description of preferred embodiments, it is noted that it is limited only by the claims hereto. For example, the important feature of providing comparable parameter variables may be utilized without some of the other techniques as disclosed. For example, instead of obtaining difference values (e.g., $QT_{dif}$ and $ACT_{dif}$), the parameter values may be compared on another basis. Further, actual rate control may be achieved by changing pacing interval directly to the point on the reference, or correlation curve corresponding to the sensed parameter, rather than simply incrementing or decrementing by a given amount. Such variations are programmable and are within the scope of the invention.

What is claimed is:

1. A pacing system having rate controllable pulse generator means for generating pacing pulses, first sensor means for developing first signals indicating a first pacing rate, second sensor means for developing second signals indicating a second pacing rate, and rate control means for determining desired pacing rate and controlling the rate of said pulse generator means, said rate means further comprising algorithm means for determining (a) from each of said first and second sensor means signals a respective indicated direction of rate change and amount of rate change, and (b) for determining said desired pacing rate as a function of said directions and amounts.

2. The pacing system as described in claim 1, comprising a lead having a first end with an electrode adapted for placement in the patient's ventricle, the other end being electrically connected to said pulse generator means, said first sensor means including said lead and comprising means for detecting the QT interval, and wherein said second sensor means provides an output indicative of the patient's physical activity.

3. The pacing system as described in claim 1, wherein said first signals indicate a physiological rate reflective of the physiological state of said patient, and wherein said second signals indicate a fast rate reflective of a relatively fast response to patient conditions compared to said physiological rate.

4. The pacing system as described in claim 1, wherein said second sensor means has a relatively fast response to patient conditions compared to the response of said first sensor means.

5. The pacing system as described in claim 3, wherein said algorithm means comprises means for comparing said physiological and fast rates, means for deriving a rate difference indication therefrom, and means for determining pacing rate as the physiological rate plus an increment of rate which is a function of said rate difference.

6. The pacing system as described in claim 1, wherein said algorithm means provides a signal for changing pacing rate by a predetermined step when both said first and second sensor signals indicate a rate change in the same direction.

7. The pacing system as described in claim 6, wherein said algorithm determining means has means for comparing said amount indications when said rate change directions are opposite, and means for choosing the direction of rate change on the basis of said amounts comparison.

8. The pacing system as described in claim 1, comprising means for generating first reference data for correlating said first signals and desired pacing rate and second reference data for correlating said second signals and desired pacing rate, and wherein said algorithm means comprises means for comparing said first signals with said first reference data to provide a first difference;

means for comparing said second signals with said reference data to provide a second difference; and means for comparing said first and second differences to determine said desired pacing rate.

9. The pacing system as described in claim 1, comprising means for automatically adjusting said second signals to indicate a pacing rate closer to that indicated by said first signals.

10. The pacing system as described in claim 1, wherein said algorithm means comprises means for comparing the respective indicated directions of rate change and the indicated amounts of rate change, and further comprises means for reducing the indicated amount of change determined from said second signals relative to said first signals.

11. The pacing system as described in claim 1, wherein each pacing cycle said algorithm means selects which of said sensor signals indicates a preferred rate change, and determines rate change in accordance with the selected rate change.

12. A pacemaker system adapted for implantation in the body of a patient, comprising:

pulse generator means adapted to be rate controlled for generating pacing stimulus pulses;

at least first and second sensor means for generating respective first and second pacing rate signals correlative of desired pacing rates;

indicator means for deriving from each of said pacing rate signals an indication for direction of desired change of pacing rate and an indication of amount of desired change of pacing rate;

rate determining means for determining pacing rate as a predetermined function of said direction and amount indications of each respective sensor means; and rate control means for controlling said pulse generator means in accordance with said determined pacing rate.

13. A method of pacing utilizing a rate responsive pacing system adapted to provide stimulus pulses to a patient's heart at a rate within a predetermined range which is responsive to one or both of a first physiological control parameter and a second fast response control parameter, said system having means for periodically obtaining signals reflective of said control parameters and correlating means for correlating each parameter to a respective indication of desired pacing rate, comprising:
   a) correlating one of said parameter signals so as to adjust its influence relative to the other control parameter signal, whereby pacing rate is primarily determined by said first parameter signal; and
   b) comparing said respective pacing rate indications and determining pacing rate as a function of said comparison each pacing cycle.

14. The method as described in claim 13, wherein said comparing step comprises establishing a parameter control reference point for each respective parameter each time said control parameters are obtained, each reference point representing pacing rate as a function of the respective parameter signal.

15. The method as described in claim 14, comprising comparing for each pacing cycle each control parameter with the reference point established during the prior cycle, and establishing a difference value therefrom, and said comparing step comprises comparing the difference values so obtained for the two respective parameters.

16. The method as described in claim 15, comprising automatically introducing a correction factor to said second control parameter whenever there is a difference between such control parameter and its corresponding reference point.

17. The method as described in claim 14, comprising generating said parameter control reference points in accordance with a predetermined reference curve for each respective parameter, and adjusting each said reference curve when a predetermined condition exists at at least one pacing rate within said range.

18. The method of claim 13, comprising obtaining QT interval as said first parameter and an activity count as said second parameter.

19. The method of claim 13, comprising sensing patient heartbeat, and obtaining both said first and second parameters from the sensed heartbeat.

20. The method of claim 19, comprising obtaining QT interval as said first parameter and T wave amplitude as said second parameter.

21. A pacing system having pulse generator means for delivering stimulus pulses and rate adjusting means for adjusting the rate of delivery of said stimulus pulses, slow physiological sensor means for generating a relatively slow response signal representative of desired physiological pacing rate and at least a second fast sensor means for generating a fast response signal having a faster response than said physiological signal to changing patient circumstances such as activity and the like and which is representative of pacing rate, said pacing system being characterized by:
   slow means for deriving a physiological rate indication from said slow signal;
   fast means for deriving a fast rate indication from said fast signal;
   means for comparing said physiological and fast rate indications;
   means for determining a rate factor as a function of said comparing;
   means for determining desired pacing rate as said physiological rate indication modified by said rate factor; and
   means for causing said rate factor to move in a direction so as to reduce its modifying effect.

22. The pacing system as described in claim 21 wherein said fast sensor means comprises an activity sensor, and said slow sensor means comprises means for obtaining QT interval.

23. The pacing system as described in claim 21, wherein both said slow means and said fast means comprise means for obtaining patient heartbeat signals and means for deriving signals representative of desired pacing rate from said heartbeat signals.

24. A pacemaker system adapted to continuously vary the rate of generated pacing pulses as a function of sensed patient conditions, and having at least first and second sensors for obtaining signal indications of pacing rate, said sensors having relatively high and low respective rates of response to changing patient conditions, the system having rate determining means characterized by:
   reference means for determining a sensor rate reference for each of said sensors corresponding to each pacing interval at which stimulus pulses are generated;
   difference means for determining a difference value for each sensor for each pacing interval, each said difference value reflecting the signal of each said sensor compared to the corresponding sensor rate reference for the prior interval;
   comparing rate means for comparing the difference values of each of said sensors; and
   rate means for determining rate change as a function of said comparison of difference values.

25. The pacemaker system of claim 24, comprising means for coupling said sensor rate references within a predetermined rate range.

26. The pacemaker system of claim 25, comprising means for setting the maximum output of each of said sensor to be produced at the upper limit of said rate range (URL) and at about maximum patient exercise and stress.

27. The pacemaker system of claim 24, comprising means of adjusting the relative influence of the signals of said sensors in determining rate change.

28. The pacemaker system of claim 24, wherein said rate means comprises step means for determining the step size of said rate change, said step size being variable with pacing interval.

29. The pacemaker system of claim 24, comprising means for periodically adjusting the fast rate response signal when at least a predetermined difference value exists between said fast signal and its corresponding reference value.

30. The pacemaker system of claim 24, wherein said reference means comprises adjustment means operative under predetermined patient conditions for adjusting the determined references for at least one of said sensors.

31. A pacemaker system adapted to continuously vary the rate of generated pacing pulses as a function of sensed patient conditions, having rate means for controlling pacing rate over a predetermined range of rates in response to a determination of rate change, said means for controlling comprising:
   first means for developing a first indicator of pacing rate based on a first sensed parameter;

second means for developing a second indicator of pacing rate based on a second sensed parameter which is a relatively faster-response parameter compared to said first parameter;

said second means having conversion means for converting said second indicator so that it has a proportionately lesser influence relative to said first indicator; and algorithm means for comparing said first indicator and said converted second indicator and for determining change in pacing rate as function of said comparing.

32. The pacemaker system as described in claim 31, wherein said algorithm means is operative each pacing cycle and further comprises means for determining the amount of rate change indicated by each of said indicators.

33. The pacemaker system as described in claim 31, wherein said first means comprises means for developing a signal representative of a QT time interval, and said second means comprises means for developing a signal representative of patient activity, and wherein said conversion means converts said activity signals so that said second indicator is representative of a time interval comparable to said QT interval.

34. The pacemaker system as described in claim 31, wherein said algorithm means comprises means for comparing the magnitudes of said first indicator and said converted second indicator, and comprises logic means for determining the direction of rate increase as a function of said compared magnitudes when said indicators indicate respective different directions of rate change.

35. The pacemaker system as described in claim 31, wherein said algorithm means performs said comparing periodically, and comprises means for incrementing or decrementing rate by a selected predetermined amount.

36. The pacemaker system as described in claim 31, wherein said first parameter provides a relatively slow physiological response to patient conditions and said second parameter provides a relatively fast response to patient conditions.

37. The pacemaker system as described in claim 36, wherein said first parameter is QT interval, and said second parameter is activity.

38. The pacemaker system as described in claim 36, wherein said second parameter is derived from the patient T wave.

39. The pacing system as described in claim 31, wherein said conversion means converts said second indicator to have a lesser influence relative to said first indicator throughout said predetermined range.

40. The pacing system as described in claim 31, wherein said conversion means performs the function of converting said second rate indicator generally to a lower rate than the rate indicated by said first rate indicator.

41. A pacemaker having pulse generator means for delivering stimulus pulses and rate adjusting means for adjusting the rate of delivery of said pulses, first sensor means for generating a first response signal representative of desired pacing rate and at least a second sensor means for generating a second response signal representative of the desired pacing rate, said pacemaker being characterized by:

a) first rate means for deriving a first rate change indication from said first response signal; second rate means for deriving a second rate change indication from said second response signal; and b) algorithm means operative each pacing cycle for comparing said rate change indications and for selecting one of said rate change indications, and rate means for incrementing or decrementing rate as a predetermined function of said selected rate indication.

42. The pacemaker as described in claim 41, wherein said algorithm means is further characterized by having means for automatically decreasing rate changes indicated by said first response signal.

43. The pacing system as described in claim 41, wherein one of said rate means comprises influence means for adjusting its rate change indication relative to the other rate change indication, whereby one of said response signals normally has greater influence than the other on determining rate changes.

44. A pacing system having pulse generator means for delivering stimulus pulses and rate adjusting means for adjusting the rate of delivery of said stimulus pulses, first sensor means for generating a first signal representative of a first desired pacing rate and at least a second sensor means for generating a second signal representative of a second pacing rate, said pacing system being characterized by:

first rate indication means for deriving a first rate indication from said first signal;

second rate indication means for deriving a second rate indication from said second signal;

said rate adjusting means having comparing means for comparing said first rate indication and said second rate indication to provide a rate control signal for control of said rate adjusting; and drift means for changing said second rate indication in a direction to reduce its influence relative to said first rate indication in said comparison.

45. The pacing system as described in claim 44, wherein said first sensor means generates a relatively slow response signal representative of a physiological pacing rate and said second sensor means generates a fast response signal having a faster response than said physiological signal.

46. The pacing system as described in claim 45, wherein said drift means changes said second rate indication by a fixed amount once every predetermined time period.

47. The pacing system as described in claim 46, wherein said drift means changes only a second rate indication which is false positive compared to said first rate indication.

48. The pacing system as described in claim 46, wherein said drift means corrects for second rate indications which are false negatives compared to said first rate indications.

49. A pacemaker system having means for providing stimulus pulses to a patient's heart at a rate which is responsive to one or both of a first physiological parameter and a second relatively faster-response parameter, said system having sensor means for obtaining signals reflective of said parameters and correlation means for correlating each of said parameters with a respective correlation function to respective first and second indications of pacing rate, said correlation means further comprising influence means for setting the influence of said parameter signals relative to each other so that pacing rate is primarily determined by said physiological signal, and having comparing means for comparing said first and second pacing rate indications and means for determining pacing rate as a function of said comparison.

* * * * *